(12) United States Patent
Subramanian et al.

(10) Patent No.: US 10,962,528 B2
(45) Date of Patent: Mar. 30, 2021

(54) BLUE FLUORESCENT PROTEIN MONOMERS AND USES THEREOF

(71) Applicant: WISYS TECHNOLOGY FOUNDATION, INC., Madison, WI (US)

(72) Inventors: Ramaswamy Subramanian, Bangalore (IN); Swagatha Ghosh, Kolkata (IN); Wayne Ford Schaefer, West Bend, WI (US)

(*) Notice: Subject to any disclaimer, the term of this patent is extended or adjusted under 35 U.S.C. 154(b) by 15 days.

(21) Appl. No.: 16/065,277

(22) PCT Filed: Dec. 20, 2016

(86) PCT No.: PCT/US2016/067752
§ 371 (c)(1),
(2) Date: Jun. 22, 2018

(87) PCT Pub. No.: WO2017/112658
PCT Pub. Date: Jun. 29, 2017

(65) Prior Publication Data
US 2019/0271690 A1    Sep. 5, 2019

Related U.S. Application Data

(60) Provisional application No. 62/270,888, filed on Dec. 22, 2015.

(51) Int. Cl.
| | | |
|---|---|---|
| C07K 14/46 | (2006.01) | |
| C07K 14/435 | (2006.01) | |
| C07K 14/00 | (2006.01) | |
| G01N 33/533 | (2006.01) | |
| G01N 33/566 | (2006.01) | |
| G01N 33/53 | (2006.01) | |

(52) U.S. Cl.
CPC .......... *G01N 33/533* (2013.01); *C07K 14/00* (2013.01); *C07K 14/43595* (2013.01); *C07K 14/461* (2013.01); *G01N 33/53* (2013.01); *G01N 33/566* (2013.01)

(58) Field of Classification Search
CPC .................. C07K 14/461; C07K 14/00; C07K 14/43595; G01N 33/533; G01N 33/582; G01N 33/53; G01N 33/566
See application file for complete search history.

(56) References Cited

U.S. PATENT DOCUMENTS 9,383,366 B2 * 7/2016 Schaefer ............. G01N 33/582
2014/0027296 A1 1/2014 Farooq et al.

OTHER PUBLICATIONS

Markwardt et al., An Improved Cerulean Fluorescent Protein with Enhanced Brightness and Reduced Reversible Photoswitching. PLoS One. 2011, vol. 6(3):e17896.
Schaefer et al., Localization and seasonal variation of blue pigment (sandercyanin) in walleye (Sander vitreus). Can. J. Fish. Aquat. Sci. 2015, vol. 72, p. 281-289.
Ghosh et al., Blue protein with red fluorescence. Proc Natl Acad Sci USA, Oct. 2016, vol. 113(41), p. 11513-11518.
International Search Report and Written Opinion from PCT/US2016/067752, dated May 5, 2017, 21 pages.

* cited by examiner

*Primary Examiner* — Padmavathi Baskar
(74) *Attorney, Agent, or Firm* — Quarles & Brady LLP

(57) ABSTRACT

Provided herein are monomeric variants of Sandercyanin fluorescent protein (SFP) including those monomeric SFP variants set forth in SEQ ID NO:2-6 and SFP variants with increased brightness. Also provided herein are methods of making and using fluorescent probes comprising such monomeric variants, where the fluorescent probes have specificity for desired targets.

5 Claims, 28 Drawing Sheets

Specification includes a Sequence Listing.

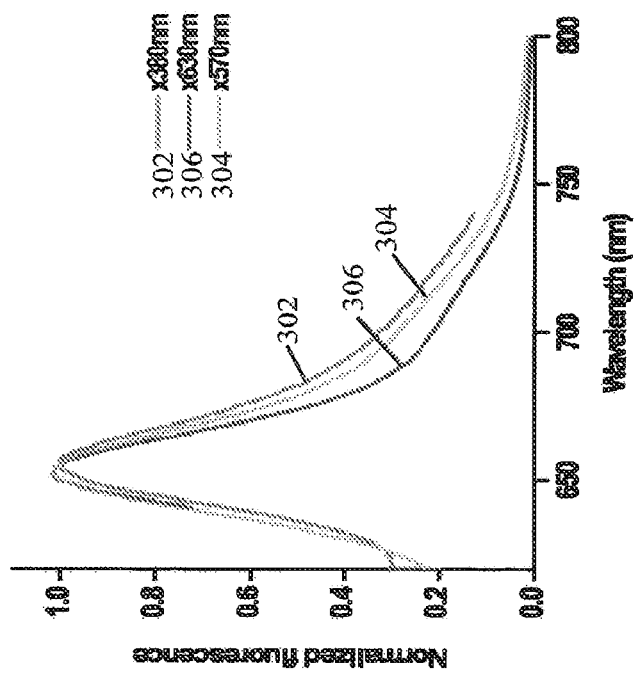
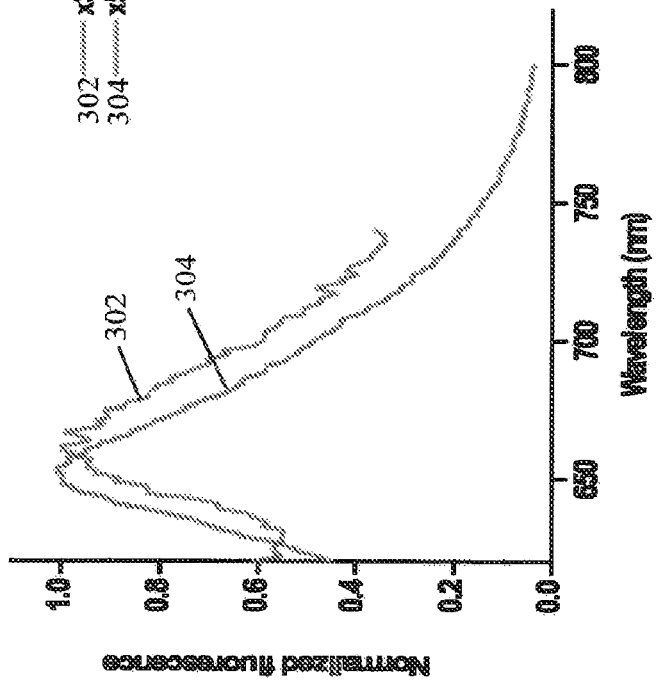
FIGS. 3A-3E

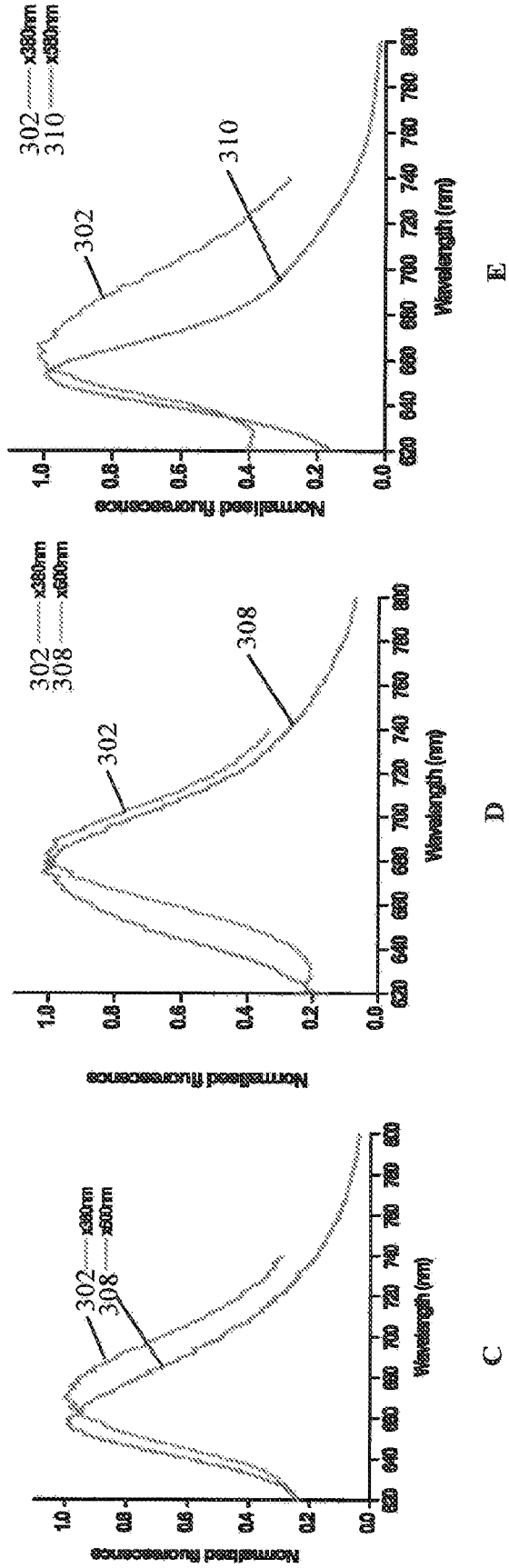
FIGS. 3A-3E, CONTINUED

FIG. 4

Amino acid sequence of wild-type Sandercyanin with signal peptide

MNAIQVISLTLLSVLAAKAMFIKPGRCPKPAVQEDFDAARYLGVWYDIQRLPNKFQKGECATA
TYSLSPGVGFSVFNRERLANGTIKSVIGSAIAEDPCEPAKLQFFHENAAPVPYWVLSTDYDNYA
LVYSCINLGASHAAYASIVSRQPTLPEETIKKLQGTMSSFGVGVDTLLTNQDAAYCSAMAQ
(SEQ ID NO:1)

Amino acid sequence of wild-type Sandercyanin without signal peptide

MFIKPGRCPKPAVQEDFDAARYLGVWYDIQRLPNKFQKGECATATYSLS
PGVGFSVFNRERLANGTIKSVIGSAIAEDPCEPAKLQFFHENAAPVPYWVL
STDYDNYALVYSCINLGASHAAYASIVSRQPTLPEETIKKLQGTMSSFGVG
VDTLLTNQDAAYCSAMNQ (SEQ ID NO:31)

19 Amino acid sequence of Sandercyanin signal peptide

MNAIQVISLTLLSVLAAKA (SEQ ID NO:32)

A  Construct design for expression of secretory SFP using mammalian cells

MASMAAVLTWALALLSAFSATQA
SEQ ID NO:29

ATMDYKDDDK
SEQ ID NO:30

B  Western blot confirmation of secreted SFP

1. Negative control (Vector only).
2. SFP Wild type
3. SFP monomeric mutant (V71E)
4. Positive control for FLAG tag(≈55 Kda)

A

B

FIGS. 9A-9F
A
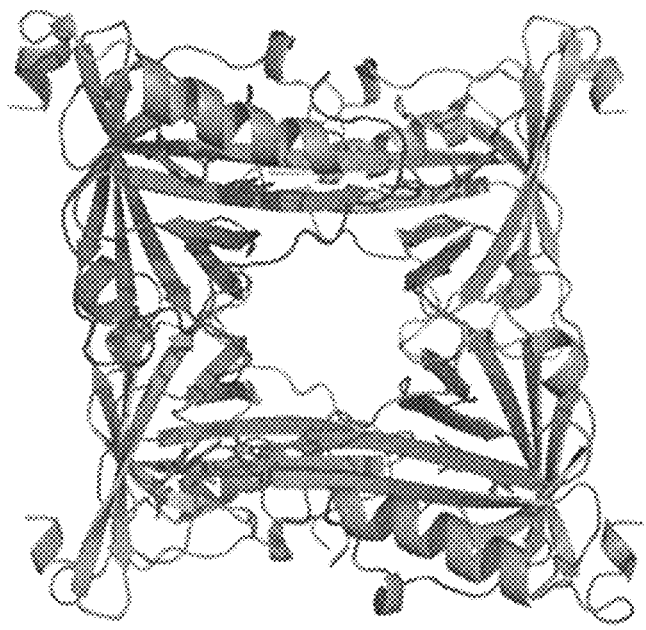
B
 

FIGS. 9A-9F, CONTINUED
C
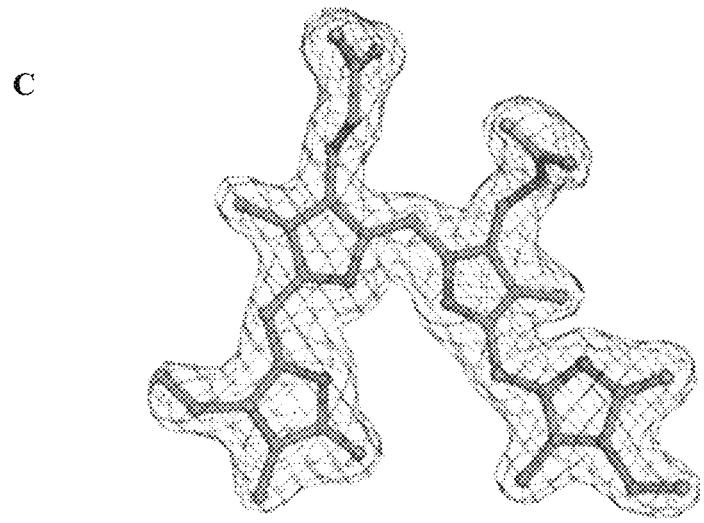
D
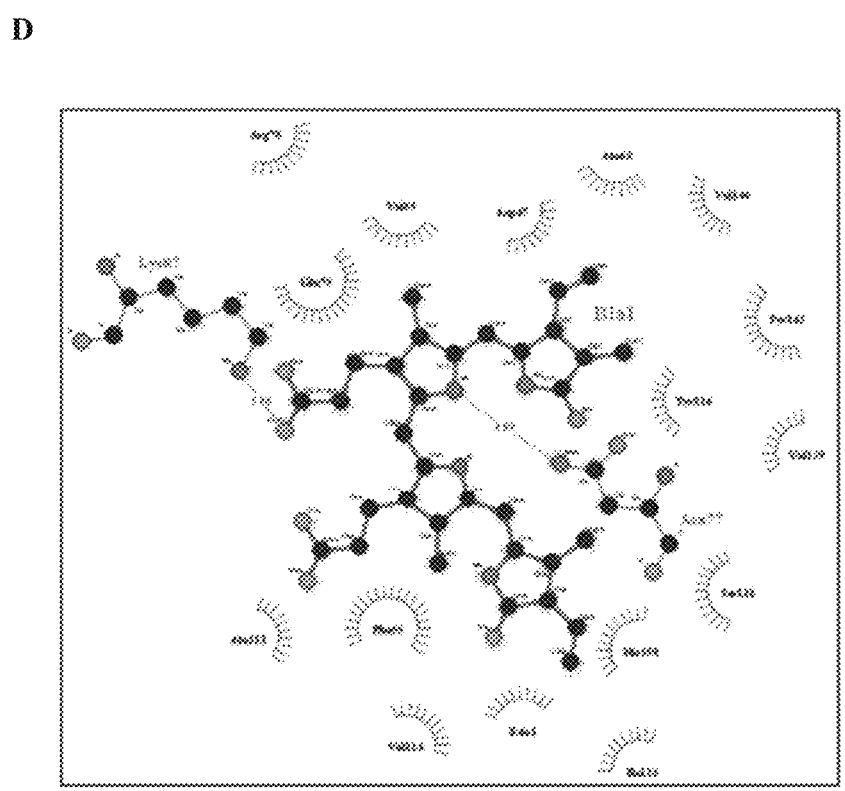

FIGS. 9A-9F, CONTINUED
E
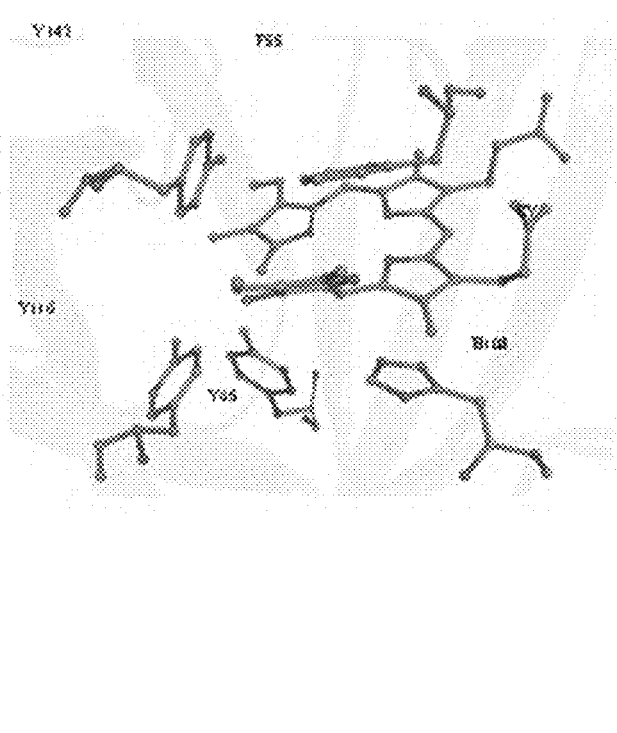
F
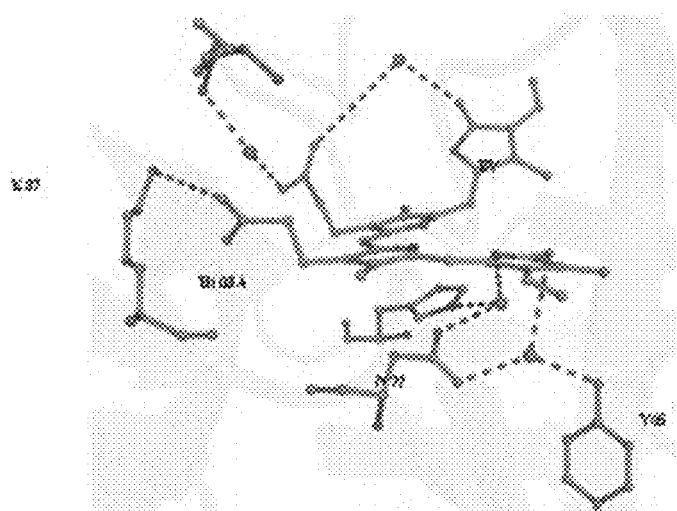

B

C

C

D

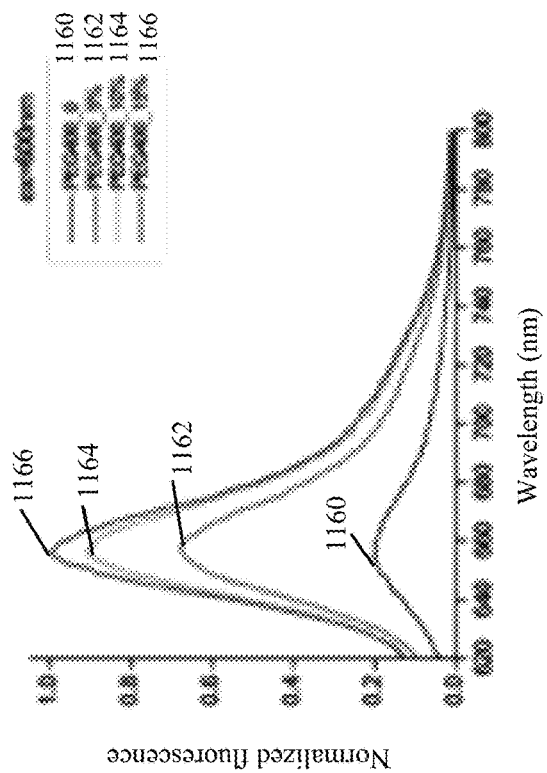
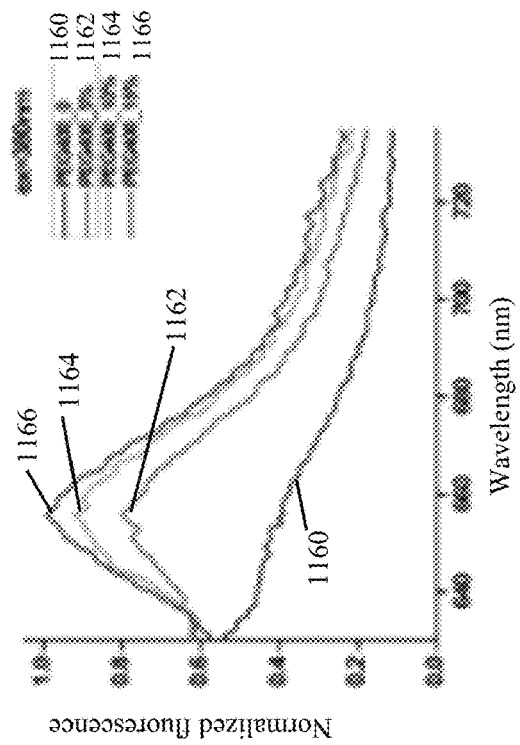
FIG. 11G

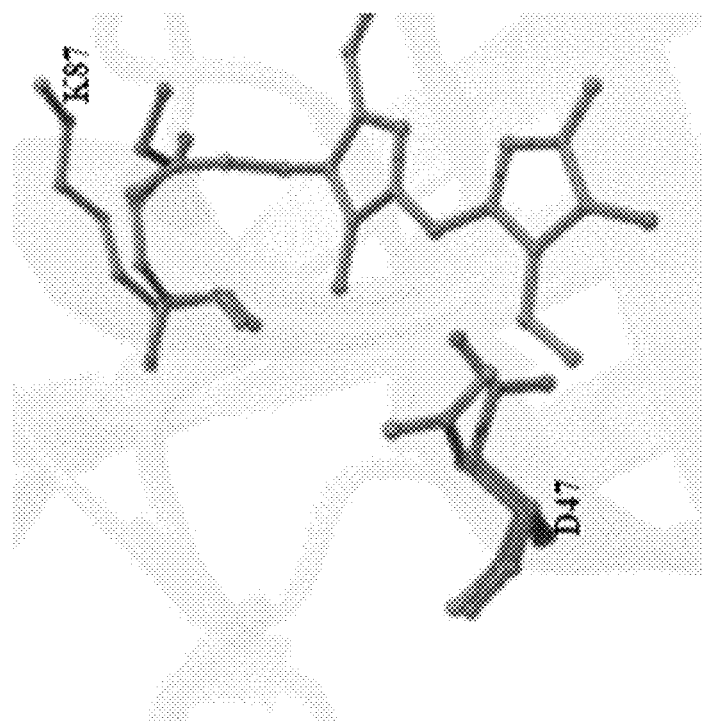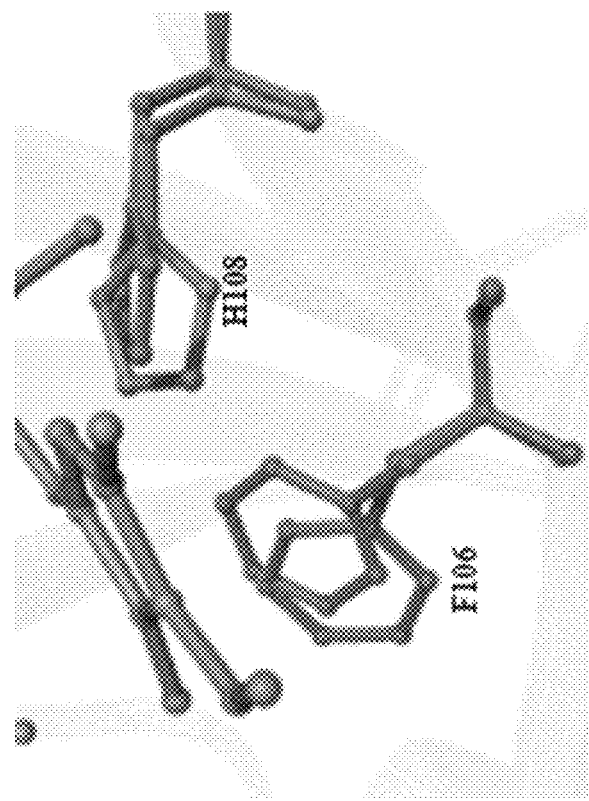
FIG. 12B

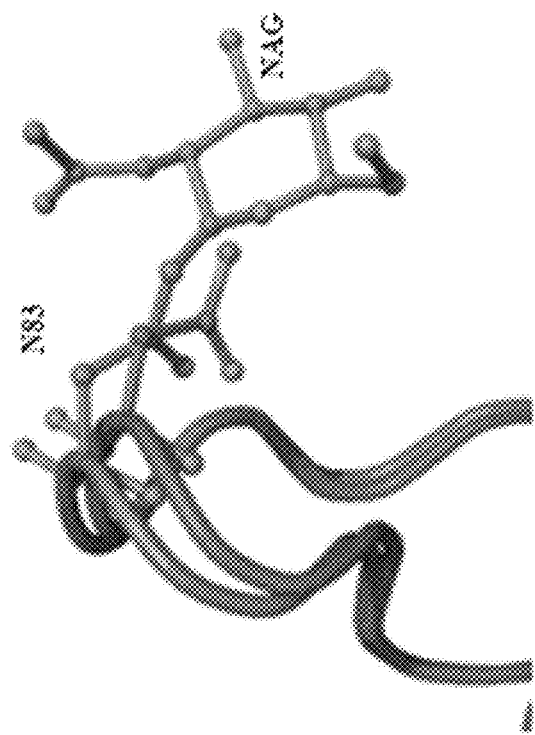
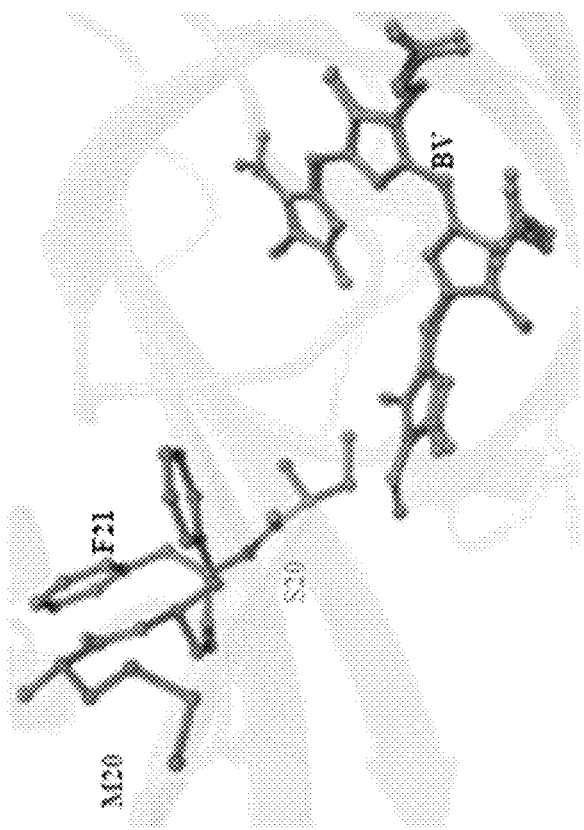
FIG. 12C

BLUE FLUORESCENT PROTEIN MONOMERS AND USES THEREOF

CROSS-REFERENCE TO RELATED APPLICATIONS

This application is a 371 U.S. National Phase entry of PCT/US2016/067752, filed Dec. 20, 2016, which claims the benefit of U.S. Provisional Application 62/270,888, filed Dec. 22, 2015, each of which is incorporated herein by reference as if set forth in its entirety.

STATEMENT REGARDING FEDERALLY SPONSORED RESEARCH OR DEVELOPMENT

Not applicable.

BACKGROUND

Bilin pigments, when associated with proteins, exhibit a wide variety of photophysical properties, i.e., intense fluorescence, photochemical interconversions, and radiationless de-excitation. Differences in the protonation state, conformation and/or ionic environment of bilin pigments can significantly alter their absorption and emission properties. In this way, the protein moiety of bili-proteins tunes the spectrum of their bilin chromophore.

Plants, some bacteria, and fungi contain phytochromes, which are self-assembling bili-proteins that act as light sensors to modulate growth and development. Phytochromes' covalently bound bilin prosthetic groups photo-isomerize upon absorption of light, enabling the protein to photo-interconvert between two distinct species, which have absorption maxima in the red and NIR region.

The optical properties of phytochromes are highly malleable, as shown by the spectral diversity of phytochromes in nature. In plants, algae and cyanobacteria, phytochromes are associated with the linear tetrapyrroles phytochromobilin (P.phi.B) or phycocyanobilin (PCB). Binding of an apo-phytochrome to the unnatural bilin precursor, phycoerythrobilin (PEB) however, affords a strongly fluorescent phytochrome known as a phytofluor that is unable to isomerize upon light absorption (Murphy. 1997, *Current Biology* 7(11):870-876). Phytofluors have been shown to be useful probes in living cells; however, addition of exogenous unnatural bilin precursors is generally necessary. Recently, a new class of phytochromes from bacteria and fungi was identified that attach a different bilin chromophore, biliverdin (BLA), to an apparently distinct region of the apoprotein (Lamparter et al., 2002, *Proceedings Natl. Acad. Sci.* 99(18): 11628-11633). These studies indicate that molecular evolution has occurred in nature to produce phytochrome mutants with novel spectroscopic properties.

Fluorescent proteins can be found in most molecular biology laboratories, and the use of fluorescent proteins has revolutionized many areas of biology. Fluorescent probes are attractive due to their high sensitivity, good selectivity, fast response and their visual detectability. For example, the jellyfish green fluorescent protein (GFP) has revolutionized cell biological studies, allowing for the visualization of protein dynamics in real-time within living cells by in-frame fusion to a gene of interest. Other fluorescent proteins known to the art include *Aequorea coerulescens* GFP (AcGFP1), a monomeric Green Fluorescent Protein with spectral properties similar to those of EGFP (Enhanced Green Fluorescent Protein); tdTomato, an exceptionally bright and versatile red fluorescent protein that is 2.5 times brighter than EGFP; mStrawberry, a bright, monomeric red fluorescent protein which was developed by directed mutagenesis of mRFP; mRaspberry, developed by directed mutagenesis of mRFP1, a monomeric mutant of DsRed; E2-Crimson, a bright far-red fluorescent protein that was designed for in vivo applications involving sensitive cells such as primary cells and stem cells; DsRed-Monomer, an ideal fusion tag which has been expressed as a fusion with a large panel of diverse proteins with diverse functions and subcellular locations; and more.

Applications of fluorescent proteins include investigation of protein-protein interactions, spatial and temporal gene expression, assessing cell bio-distribution and mobility, studying protein activity and protein interactions in vivo, as well as cancer research, immunology and stem cell research and sub-cellular localization. Fluorescent proteins have also been used to label organelles, to image pH and calcium fluxes, and to test targeting peptides (Chiesa et al. 2001, *Biochem Journal* 355: 1-12).

Despite their utility, as with any technology, existing fluorescent proteins have inherent limitations. For instance, GFP produces cytotoxic hydrogen peroxide (Cubitt et al., (1995)). Further, some fluorescent proteins are typically homo-dimers, a property that can interfere with the native function of the fused protein of interest. GFPs are also temperature and pH-sensitive and can be highly susceptible to photobleaching and oxidation. Further, GFPs are unable to fold and fluoresce in periplasmic/extra-cellular space (Jennifer et al., (2010)), hence finding limitation to be used for studying cell dynamics in the extracellular matrices.

Accordingly, there remains a need in the art for fluorescent proteins having improved characteristics as well as improved uses of such fluorescent proteins in experimental and clinical applications.

SUMMARY OF THE INVENTION

In a first aspect, provided herein is an isolated variant polypeptide of Sandercyanin fluorescent protein (SFP), where the variant has increased brightness relative to wild-type SFP of SEQ ID NO:1 or SEQ ID NO:31. The variant polypeptide can comprise an amino acid substitution at one or more of the following positions D-47, R-50, F-55, K-57, A-61, T-62, Y-65, A-63, N-77, R-78, E-79, K-87, S-88, V-89, F-106, H-108, Y-116, V-129, S-131, I-133, Y-142 and V-146 relative to SEQ ID NO:1. The variant polypeptide can comprise at least one amino acid substitution selected from the group consisting of V71E, L135E, L135F, A137E, A137F, A111E, and A111F relative to SEQ ID NO:1. The variant polypeptide can comprise SEQ ID NO:2, SEQ ID NO:3, SEQ ID NO:4, SEQ ID NO:5, SEQ ID NO:6, or SEQ ID NO:7. The variant polypeptide can exist primarily as a monomer.

In another aspect, provided herein an isolated polynucleotide encoding a variant polypeptide as provided herein. The polynucleotide can further encodes a polypeptide of interest linked to the variant polypeptide, whereby the polypeptide of interest and the variant polypeptide are expressed as a fusion protein.

In a further aspect, provided herein is a construct comprising the polynucleotide of as provided herein operably linked to a promoter.

In another aspect, provided herein is a vector comprising the construct.

In yet another aspect, provided herein is a fluorescent probe comprising a monomeric variant of SFP and a moiety having specificity for a target. The monomeric variant of SFP can comprise an amino acid substitution at one or more of the following positions relative to SEQ ID NO:1: D-47, R-50, F-55, K-57, A-61, T-62, Y-65, A-63, N-77, R-78, E-79, K-87, S-88, V-89, F-106, H-108, Y-116, V-129, S-131, I-133, Y-142 and V-146. The monomeric variant can comprise at least one amino acid substitution selected from the group consisting of V71E, L135E, L135F, A137E, A137F, A111E, and A111F relative to SEQ ID NO:1. The monomeric variant of SFP can comprise SEQ ID NO:2, SEQ ID NO:3, SEQ ID NO:4, SEQ ID NO:5, SEQ ID NO:6, or SEQ ID NO:7. The moiety can be selected from the group consisting of an antibody, a polypeptide, a peptide, and an enzyme. The probe can emit a fluorescent signal. The target can be a biomolecule.

In another aspect, provided herein is a method for detecting a target, the method comprising: (a) contacting a fluorescent probe to a sample under conditions suitable for binding of the probe to the target if present in the sample; (b) exposing the contacted sample to light having a wavelength from about 350 to about 690 nm; and (c) detecting fluorescence emitted from the probe.

In any embodiment of the variant SFP, the variant SFP polypeptide may be lacking the signal peptide of SEQ ID NO:32.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIGS. 3A-3E are normalized fluorescence spectra of monomeric SFP variants in complex with biliverdin at 380 nm (green 302), 570 nm (red/orange 304), 580 (red 310), 630 nm (maroon 306), and 600 (red 308). (A) V71E (B) L13E (C) A137E (D) FH88insGG and (E) VP95insGG.

FIG. 4 is an amino acid sequences of Sandercyanin.

FIG. 5C shows overlap of wtSFP structure with mSFP1 and mSFP2. FIGS. 5D-5F show overlap of chromophore structure in wtSFP with mSFP1 and mSFP2 show D-ring flipping of biliverdin in the binding pocket.

FIGS. 9A-9F demonstrate crystal structures of apo and holo SFP. (A) Overall structure of holoSFP in the asymmetric subunit, with crystal packing in hexagonal space group P6322. (B) Structures of monomeric SFP (i and ii) with BV IXa in the ligand-binding pocket. (C) Final configuration of biliverdin (BV) in the refined structure of holoSFP. (D) Lig-plot showing residue surrounding biliverdin (labeled as Bla1) in the ligand-binding pocket. (E) Interaction of aromatic residues with pyrrole rings of BV in the binding pocket. (F) Detailed view of ionic and water mediated H-bond interactions of BV with its surrounding residues in the ligand-binding pocket.

FIG. 10A SDS-PAGE gels showing (i) purification of recombinant SFP from inclusion bodies (ii) comparison of native and recombinant SFP.

FIGS. 10B-10C Size-exclusion chromatogram showing mono-disparity and biliverdin-induced tetramerization of purified recombinant SFP. (C) CD-spectra showing presence of secondary beta-structure and BV-induced chirality, and effect of temperature on the secondary structure of SFP.

FIG. 10D Reversal of oligomerization of SFP tetramer after photobleaching, normalized to tetramer peak.

FIGS. 11A-11I show biliverdin (BV)-inducible near-infrared fluorescence of SFP and binding studies.

FIGS. 11A-11B (A) Titration of BV with apoSFP shows enhanced red-shift in fluorescence. Labels represent 0 μM 1102, 1 μM 1104, 2 μM 1106, 5 μM 1108, 7.5 μM 1110, 10 μM 1112, 20 μM 1114, 30 μM 1116. (B) Overlap of normalized excitation (blue 1120) and fluorescence (red 1122) spectra of holoSFP, showing no or minimum spectral overlap with the blue and red-absorbance respectively.

FIGS. 11C-11D (C) Titration of apo-SFP (20 uM) with BV IXα measured at 675 nm with λex=375 nm (green) and 630 nm (red). (D) Photo-bleaching kinetics of Sandercyanin and free-biliverdin (BV).

FIG. 11E Binding of apoSFP with other tetrapyrroles monitored by fluorescence on excitation at (left) 375 nm and (right) 630 nm.

FIG. 11F Effect of hydrophobicity of solvent on fluorescence spectra of biliverdin monitored at excitation wavelengths of (left) 375 nm and (right) 600 nm. Labels are biliverdin in DMSO 1150, biliverdin in acetone 1152, biliverdin in ethanol 1154, biliverdin in benzene 1156, and biliverdin in toluene 1158.

FIG. 11G Effect of viscosity of solvent (PEG 400) on fluorescence spectra of biliverdin monitored at excitation wavelengths of (left) 375 nm and (right) 600 nm. Labels are 0% PEG400 1160, 5% PEG400 1162, 10% PEG400 1164, and 15% PEG400 1166.

FIG. 11H Effect of pH on fluorescence spectra of biliverdin monitored at excitation wavelengths of (left) 375 nm and (right) 600 nm. Labels are pH 3 1170, pH 4 1171, pH 5 1172, pH 6.2 1173, pH 7 1174, pH 8 1175, pH 8.8 1176, pH 9.5 1177, pH 10 1178, pH 10.8 1179.

FIG. 11I Spectral overlap of (top) absorbance, (middle) fluorescence and (bottom) excitation spectra of native and recombinant SFP. Labels are biliverdin 1180, recombinant SFP 1182, native SFP 1184, recombinant SFP with biliverdin 1186.

FIGS. 12A-12D show the crystal structure of apo and holo SFP.

FIG. 12A shows crystals and crystallization conditions of apo (colorless) and BLA-bound (blue) forms of native and recombinant Sandercyanin.

FIG. 12B Structural insights into the ligand binding pocket of apo (yellow) and holo SFP (cyan) showing conformational changes in amino acid near D-ring (left) and B-ring (right) of BV.

FIG. 12C Comparison of structures of native (magenta) Vs recombinant (cyan) SFP in complex with BV, showing flipping of Phe21 (left) at the N-terminal, but no effects on the position of glycosylation (right).

FIG. 12D Crystal structures showing (top) biliverdin-protein and (bottom) protein-protein interactions at the two dimer interfaces of SFP.

DETAILED DESCRIPTION OF THE INVENTION

Figures 1A, 1B, 1C, 1D:
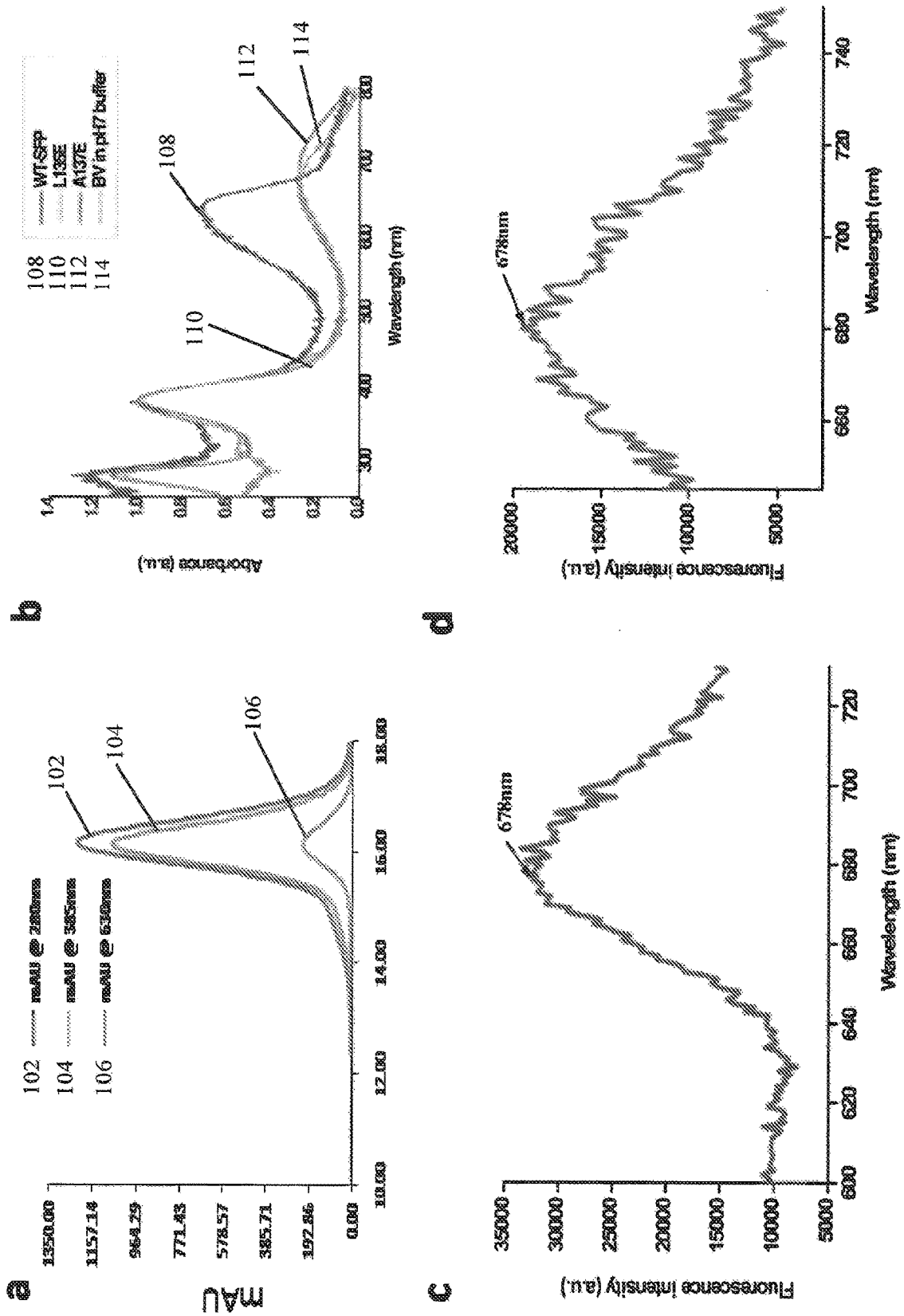
FIGS. 1A-1D present spectroscopy data for (A) absorption in milli absorption units (mAU), (B) absorbance, and (C-D) fluorescence intensity of SFP monomer. (A) Size-exclusion chromatography on S200 analytical column showing monomer protein at 280 nm (ultraviolet 102) binding to biliverdin with absorbance 385 nm (blue 104) and 630 nm (red 106). (B) Overlapped absorbance spectra of the biliverdin (BV)-bound L135E 110 and A137E 112 monomeric SFP mutants with wild type SFP 108 and free biliverdin (BV) 114.

The present invention provides polypeptide variants of wild-type Sandercyanin (wtSFP), a fluorescent blue protein derived from the mucus on the outside of walleye, *Sander vitreus*, in the Papaonga River system of Ontario (Yu et al., *Environ Biol Fish*, 82:51-58, 2008; Ghosh et al. 2016. A Blue Protein with Red Fluorescence. PNAS 113(41): 11513-11518). The term "blue walleye" refers to walleye (*Sander vitreus*) that secrete blue sandercyanin into their skin mucus. Blue walleye are not a separate subspecies of *S. vitreus* but rather are only a color variant. Sandercyanin is secreted by the fish into its skin mucus and likely functions as a photo-protectant in the northern range of walleye in North America (Schaefer et al., *Canadian Journal of Fisheries and Aquatic Sciences* 72(2):281-289, 2015). Sandercyanin is a bili-binding, lipocalin protein with a molecular mass of 87,850. It is a tetramer having a subunit molecular mass of 21,386 Daltons. SFP has absorption maxima at 280, 383, and 633 nm and has emission maxima at 678 nm on excitation at 380 nm and 630 nm (Yu et al., *Environ Biol Fish*, 82:51-58, 2008). Both excitation and emission peaks are broad and have minimal spectral overlap. See U.S. Pat. No. 9,383,366 (issued Jul. 5, 2016), which is herein incorporated by reference in its entirety.

This invention pertains to the surprising discovery that polypeptide monomers of Sandercyanin are useful for fluorescently marking a protein, cell, or organism of interest in many biochemistry, molecular biology and medical diagnostic applications. Provided herein is a monomeric form of the naturally occurring tetramer of sandercyanin (Yu et al., *Environ Biol Fish*, 82:51-58, 2008; Schaefer et al., *Canadian Journal of Fisheries and Aquatic Sciences* 72(2):281-289, 2015; Ghosh et al.). The monomer has the same bili-binding characteristics of the tetramer but is one-fourth the size of the tetramer and therefore more useful in biotechnology applications. Like the tetramer, the monomer has a large stokes shift and binds biliverdin (BLA or BV) non-covalently, which inhibits photo-bleaching of fluorescence. When biliverdin is added to the monomer, it takes on a blue color and fluoresces in far-red. Since the variant monomers taught herein do not oligomerize, they could be useful as fluorescent protein tag when fused to another protein.

In a first aspect, therefore, provided herein are novel variants of Sandercyanin fluorescent protein (SFP), wherein the variants remain monomeric. Native (wild-type) SFP has the amino acid sequence set forth in SEQ ID NO:1 (see FIG. 4) which includes a signal peptide (SEQ ID NO:32). Recombinant wild-type SFP lacking the signal peptide is defined by SEQ ID NO:31. SFP variants provided herein are derived from the naturally occurring SFP by engineering mutations such as amino acid substitutions into the reference SFP protein. As used herein, the terms "variant" and "mutant" are used interchangeably and refer to a protein that is different from a reference protein (e.g., comprising a truncation, insertion, substitution, or other variation thereof) as long as they retain the ability to fluoresce red light. For example, amino acids suspected of contributing to molecular brightness can be replaced by amino acid residues that are likely to increase molecular brightness of the fluorescent proteins. Generally, fluorescent protein variants having increased molecular brightness of bright fluorophores have advantageously higher signal-to-noise (S/N) ratios, especially in intracellular environments where auto-fluorescence can contribute to background. In addition, fluorescent protein variants having higher molecular brightness require lower laser power and allow for a reduced exposure of the cells to potentially harmful irradiation, which also reduces photo-bleaching.

As used herein, the terms "polypeptide", "peptide" and "protein" are used interchangeably and refer to amino acid polymers including, without limitation, naturally occurring amino acid polymers, artificial analogues of a naturally occurring amino acid polymer, as well as variants and modified polypeptides. Abbreviations used herein for the amino acids are those stated in *J. Biol. Chem.* 243:3558 (1968).

Wild-type Sandercyanin including the 19 amino acid signal peptide is defined by SEQ ID NO:1. In some embodiments of the present invention, the 19 amino acid signal peptide (SEQ ID NO:32) is removed and the SFP recombinant wild-type protein is SEQ ID NO:31 wherein the initial methionine of SEQ ID NO:31 corresponds to methionine 20 in SEQ ID NO:1. Therefore, one of ordinary skill in the art can map all variants taught herein relative to SEQ ID NO:1 onto SEQ ID NO:31. For clarity in labeling, variations are presented relative to wild-type SFP comprising the signal peptide (SEQ ID NO:1), but it is understood that the corresponding variations and mutations in the recombinant wild-type SFP lacking the signal peptide would have the same effect.

In some embodiments, the variant SFP comprises a polypeptide with a sequence that is at least 80% to about 100% identical to the sequence of any one of SEQ ID NOs:1-7 and 31, e.g., about 80%, 82%, 84%, 85%, 86%, 87%, 88%, 89%, 90%, 91%, 92%, 93%, 94%, 95%, 96%, 97%, 98%, 99%, and 100% identical to the sequence of any one of SEQ ID NOs:1-7 and 31.

In some cases, a fluorescent protein variant provided herein is a monomeric Sandercyanin fluorescent protein, designated mSFP, which contains an amino acid substitution at one or more of the following positions: D-47, R-50, F-55, K-57, A-61, T-62, Y-65, A-63, N-77, R-78, E-79, K-87, S-88, V-89, F-106, H-108, Y-116, V-129, S-131, I-133, Y-142 and V-146 relative to the SFP polypeptide of SEQ ID NO:1. More preferably, a mSFP provided herein comprises one or more of the following mutations relative to the wild-type SFP sequence SEQ ID NO:1: L135E, L135F, A137E, A137F, A111E, and A111F. In some cases, a mSFP provided herein comprises an amino acid sequence as set forth as SEQ ID NOs:2-7 (see Table 2 and Table 3) and has red fluorescent properties.

In one embodiment, the monomeric SFP is SFP-V71E and is or comprises the sequence of SEQ ID NO:2, wherein V71 is numbered relative to SEQ ID NO:1.

In one embodiment, the monomeric SFP is SFP-L135E and is or comprises the sequence of SEQ ID NO:3, wherein L135 is numbered relative to SEQ ID NO:1.

In one embodiment, the monomeric SFP is SFP-A137E and is or comprises the sequence of SEQ ID NO:4, wherein A137 is numbered relative to SEQ ID NO:1.

In one embodiment, the monomeric SFP is SFP-V52E and is or comprises SEQ ID NO:7, wherein V52 is numbered relative to SEQ ID NO:31, and is the same amino acid variation as V71 relative to SEQ ID NO:1.

In one embodiment, the modified monomeric SFP is SFP-L135E, FH88insGG and is or comprises the sequence of SEQ ID NO:5, wherein L135 is numbered relative to SEQ ID NO:1.

In one embodiment the modified monomeric SFP is SFP-L135E, VP95insGG and is or comprises the sequence of SEQ ID NO:6, wherein L135 is numbered relative to SEQ ID NO:1.

Any of the embodiments described herein may optionally comprise the SFP signal peptide signal sequence SEQ ID NO:32.

Preferably, mSFPs provided herein exhibit a large Stokes shift (approximately 200 nm to 300 nm) with excitation and emission at 375 nm and 675 nm, respectively. As used herein, the term "Stokes shift" refers to the difference in nanometers between the peak excitation and the peak emission wavelengths. Stokes shift is represented by ($h\nu_{EX}$-$h\nu_{EM}$), where a photon of energy $h\nu_{EM}$ is emitted and a photon of energy $h\nu_{EX}$ is excited. As used herein, "large Stokes shift" means a shift of at least 100 nm, preferably at least 100-150 nm, and more preferably approximately 200-300 nm.

Fluorophores having larger Stokes shifts are advantageous for fluorescence detection and/or imaging in biological applications because the excitation and emission photons are easier to distinguish in a sample, while fluorophores with smaller Stokes shifts exhibit greater background signal because of the smaller difference between excitation and emission wavelengths. A large Stokes shift is also advantageous for fluorescence detection and/or imaging applications because homo-FRET (fluorescence resonance energy transfer (FRET) between identical donor and acceptor fluorophores or fluorophores that are located within about 10 nm of each other) is less likely to occur. Fluorescent proteins having a small Stokes shift often lack sensitivity due to self-quenching and interference from excitation and scattered light. Examples of small Stokes shift proteins include, without limitation, green fluorescent protein (GFP)-like fluorescent proteins, which typically exhibit Stokes shifts of approximately 10 nm to 45 nm due to rigidity of the chromophore environment that precludes non-fluorescent relaxation to a ground state.

In other embodiments, the invention provides a fluorescent labeled marker for detection of a target, the marker comprising a label selected from the group consisting of Sandercyanin fluorescent protein and a fluorescent variant thereof, and a ligand configured to bind to the target. As used herein, the term "fluorescently labeled" refers to derivatizing a molecule with a fluorescent material. As used herein, the term "ligand" refers to any ligand known to the art, including, for example and without limitation, a nucleic acid probe, an antibody, a hapten conjugate, biotin, avidin and streptavidin. By "target" we mean any biomolecule or non-biomolecule. By "biomolecule" we mean any biological molecules known to the art, including, without limitation, antibodies; proteins, in particular proteins recognized by particular antibodies; receptors; enzymes or other ligands; nucleic acids (e.g., single or double stranded DNA, cDNA, mRNA, cRNA, rRNA, tRNA, etc.); various sugars and polysaccharides; lectins; and the like.

In some cases, provided herein is a method for producing an isolated recombinant protein comprising introducing DNA encoding an exogenous protein into the organism, culturing the organism in an enclosed system, harvesting the organism, and isolating the recombinant protein from the organism, wherein the recombinant protein is variant of mSFP. The DNA may contain a promoter that is functional in the organism.

By "isolated" we mean a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature.

For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature.

The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

In a further aspect, there is provided an expression vector comprising suitable expression control sequences operably linked to a DNA molecule. The DNA may be inserted into a recombinant vector, which may be any vector that may be conveniently subjected to recombinant DNA procedures. The choice of vector will often depend on the host cell into which it is to be introduced. Thus, the vector may be an autonomously replicating vector, e.g., a vector which exists as an extrachromosomal entity, the replication of which is independent of chromosomal replication, e.g., a plasmid.

Alternatively, the vector may be one which, when introduced into a host cell, is integrated into the host cell genome and replicated together with the chromosome(s) into which it has been integrated. As used herein, the term "recombinant" refers to a biomolecule that has been manipulated in vitro, e.g., using recombinant DNA technology to introduce changes to a genome.

The term "operably linked" means that the regulatory sequences necessary for expression of the coding sequence are placed in the DNA molecule in the appropriate positions relative to the coding sequence so as to effect expression of the coding sequence. The same definition is sometimes applied to the arrangement of coding sequences and transcription control elements (EG promoters, enhances, and termination elements) in an expression vector. This definition is also sometimes applied to the arrangement of nucleic acid sequences of a first and a second nucleic acid molecule wherein a hybrid nucleic acid molecule is generated.

Also provided herein is a fusion compound, preferably a fusion protein, comprising a protein of interest fused to mSFP. The type of protein of interest with which the mSFP is fused is not particularly limited. Preferred examples may include proteins localizing in cells, proteins specific for intracellular structures, in particular intracellular organelles and targeting signals (e.g., a nuclear transport signal, a mitochondrial pre-sequence and the like). The obtained fusion protein wherein the mSFP variant is fused with a protein of interest is allowed to be expressed in cells. By monitoring a fluorescence emitted, it becomes possible to analyze the activity, localization, processing, or dynamics of the protein of interest in cells. That is, cells transformed or transfected with DNA encoding the mSFP are observed with the fluorescence microscope, so that the activity, localization, processing and dynamics of the protein of interest in the cells can visualized and thus analyzed.

mSFPs provided herein are particularly useful as labeling substances or markers (labels, tags), preferably in biological and/or medicinal imaging. The importance of recombinant proteins for modern medical applications and therapy is known in the art. Recombinant production methods for bacteria are well developed and many important commercial proteins are produced in bacterial prokaryotic systems. In some cases, a monomeric Sandercyanin fluorescent protein is useful as a marker to identify transfected cells. For example, red fluorescence (NIR range) of mSFPs makes them promising markers for deep tissue imaging in vivo. Because biliverdin is present in mammalian cells as a product of heme-degradation, the intrinsic fluorescence can be observed by co-expressing a mSFP and a protein of interest as a fusion protein. Further, because biliverdin is a non-covalent chromophore, it will replenish fluorescence after photo-bleaching on adding external biliverdin.

In still other embodiments, a mSFP as provided herein can be used as in vitro or in vivo labels in a manner analogous to the use of GFP or GFP-like fluorescent proteins. Uses of GFP and GFP-like fluorescent proteins are well known to those of skill in the art (see e.g., U.S. Pat. No. 5,491,084 which describes uses of GFP).

In another aspect, provided herein is a fluorescent probe and a method of preparing a fluorescent probe. As used herein, the term "probe" encompasses any probe known to the art, including, for example and without limitation, antibodies, proteins and enzymes. The probe comprises a mSFP attached to a probe for detecting a specific target wherein, when excited, the probe emits a fluorescent signal. By "fluorescent," we mean the probe exhibits fluorescence.

Based on the disclosure provided herein, one of skill will readily appreciate that there are numerous other uses to which mSFPs provided herein can be applied.

As used herein "molecular brightness" or "brightness" refers to the ratio of the quantum yield to the molar extinction coefficient of the protein. Quantum yield is defined as the ratio of the number of photons emitted to the number of photons absorbed. As used herein "fluorescence emission" refers to the quantum yield of the fluorophore which is the ratio of the number of photons emitted to the number of photons absorbed. Therefore, if two proteins have the same molar extinction coefficient, the protein with the higher quantum yield will have the higher brightness.

In some cases, it will be advantageous to modify monomeric SFP provided herein in order to increase brightness of the fluorescent proteins. Monomeric SFP may be modified by substituting one or more amino acids within the wild-type SFP sequence, addition of amino acids into the wild-type SFP sequence, or deletion of amino acids from the wild-type SFP sequence. The sequence of wild-type SFP is defined by SEQ ID NO:1

Strategies utilized to increase brightness may include modifying one or more amino acids of monomeric SFP in order to increase hydrophobicity in the binding pocket, increasing binding affinity of biliverdin, covalent binding of the ligand, restriction of the conformational degrees of freedom of biliverdin, increasing 'flipping' of the D-ring of biliverdin, increasing loop size proximal to the biliverdin D-ring. By "flipping phenomenon", we mean the isomerization of the D-ring of biliverdin around the C15-C16 bond. Strategies to increase brightness are described in detail in Example 4.

Methods

In another aspect, provided herein is a method of using a fluorescent probe to detect a target. The method can comprise or consist essentially of providing a fluorescently labeled ligand comprising a mSFP as provided herein (the label) and a ligand for binding the target; contacting the target with the labeled ligand; allowing the labeled ligand to bind to the target; subjecting the labeled ligand and target to light having a wavelength which excites the label (e.g., from about 350 to about 690 nm); and detecting fluorescence.

In another aspect, provided herein are methods of using a mSFP in multi-photon, multi-color applications. For example, provided herein is a method of dual-color cell imaging of live cells. Such methods are useful for investigating intracellular protein-protein and other molecular interactions in living cells.

Fluorescence may be detected and measured using any appropriate technique known to the art, including without limitation, fluorescence microscopy, flow cytometry, or fluorescence activated cell sorting (FACS). For example, fluorescence may be detected by tracking, quantifying, and sorting of cells labeled with a mSFP using flow cytometry or FACS.

Also provided herein are methods for attaching a mSFP to a non-biological molecule or substrate. As used herein, "non-biological molecule or substrate" means a synthetic compound or medical device, implant, and the like. Thus, for example and without limitation where it is desired to associate a specific medical device or implant with a particular manufacturer, distributor, or supplier, the Sandercyanin label, or a fragment of the protein label, can be attached to the subject article. Later "development" (e.g., by addition of a second component such as bilin or apoprotein) and exposure to an appropriate light source will provide a fluorescent signal identifying the article as one from a source of such labeled articles.

Advantages of mSFPs

Monomeric SFP offers many advantages over oligomeric fluorescent proteins.

First, smaller sized monomeric proteins are well suited for use as fusion tags. Although, the wild type SFP is tetramer with a subunit molecular mass of about 21 kDa, based on the site directed mutagenesis on the oligomeric interface we have engineered mSFPs that retain the fluorescent properties of wild type SFP but notably the molecular mass of the mSFP variants provided herein (about 18.6 kDa) is smaller than the currently available smallest GFP variant (about 26 kDa).

Second, the photostability of mSFP is compatible for use as a fluorescent protein. For instance, the smaller size of this protein enables it to be easily expressed and manipulated for use.

Third, mSFP variants can be expressed as a fusion to another protein, and will remain fluorescent and should not interfere with the protein's folding, cleavage, and maturation processes. Protein folding of mSFP is not impaired by fusion to other polypeptides.

Fourth, mSFP's sensitivity to environmental changes is also compatible with uses as a fluorescent protein.

Fifth, the large Stokes Shift of monomeric SFP provides greatly improved detectability. For instance, mSFP's emission in red emits very little scattering, making the monomeric fluorescent protein well suited for, among other things, deep tissue imaging and other biological applications.

Sixth, SFP evolved in a eukaryotic vertebrate organism, not a prokaryotic bacterial or algal organism. Therefore, it will likely be more compatible for use in humans.

Monomeric SFP acts as a non-covalent ligand, making it easy to regenerate after photo-bleaching. The protein's ability to turn on when required by adding the ligand (especially in extracellular applications) provides a huge advantage over conventional fluorescent proteins.

Monomeric SFP's excitation and emission wavelength, number of spectral peaks, quantum efficiency, extinction coefficient, Stokes shift, degree of aggregation and oligomerization, time to maturation, and ability to participate in fluorescence resonance energy transfer all support these advantages.

Commercial Applications of Monomeric Sandercyanin Fluorescent Proteins

Biomarker: Uses of the various Sandercyanin-labeled biomolecules will be readily apparent to one of skill in the art. Thus, for example, Sandercyanin-labeled nucleic acids can be used as probes to specifically detect and/or quantify the presence of the complementary nucleic acid in, for example, a Southern blot. In various embodiments, the Sandercyanin-labeled biomolecules can be expressed in fusion with a heterologous protein and in this context can act as a reporter molecule (e.g., when contacted with a (native or exogenous) bilin) to identify gene activations, protein expression, and/or protein localization within a cell. Similarly, the Sandercyanin-labeled biomolecules can act to identify particular cell populations in cell sorting procedures.

Fluorescent Probe: In another embodiment, the Sandercyanin protein can be used for probing protein-protein interactions. Protein-protein interaction between two proteins of interest (e.g., protein X and protein Y) is identified following their co-expression as translational fusions with the Sandercyanin protein in constructs 1 (donor) and 2 (acceptor) using fluorescence energy transfer from the shorter wavelength-absorbing donor species to the longer wavelength-absorbing acceptor species. In a preferred embodiment, the fluorescent phytochrome species are selected to have good spectral overlap. Proximity caused by the protein-protein interaction between the translational fused proteins X and Y will then permit fluorescence energy transfer thereby providing an indication of proximity between protein X and protein Y.

In an illustrative application, a yeast or *E. coli* strain containing donor construct 1, engineered to produce a fluorescent chimeric protein "bait" with a known cDNA sequence, is co-transformed, simultaneously or sequentially, with a "prey" cDNA library (i.e., plasmid or phage). The "prey" cDNA library is constructed using acceptor construct 2 for expression of apoprotein-protein fusions which yield fluorescent tagged protein products in the presence of the correct bilin. Co-transformation events that express "prey" proteins in the library that interact with the expressed "bait" polypeptide can be identified by illuminating the shorter wavelength absorbing donor phytofluor species and viewing emission from the longer wavelength acceptor phytofluor emitting species. Actinic illumination for this screen can either be obtained with a quartz halogen projector lamp filtered through narrow bandpass filters or with a laser source and fluorescence detection of colonies using digital imaging technology. Fluorescent activated cell sorting (FACS) can also be used to identify cells co-expressing interacting donor and acceptor proteins.

In another illustrative application, chimeric apoprotein-protein X cDNA (where protein X is any protein of interest) are expressed in transgenic eukaryotes (yeast, plants, Drosophila, etc.) in order to study the subcellular localization of protein X in situ. Following feeding of exogenous bilin, subcellular localization can be performed using fluorescence microscopy (e.g., laser confocal microscopy).

Other Commercial Embodiments of the Invention

Monomeric SFP's unique ability to be excited at a relatively low and distant wavelength with respect to its emission wavelength lends itself to many commercial applications. Specifically, monomeric SFP can be used for imaging proteins, studying protein dynamics and other molecular complexes inside cells, which allows it to be used in a variety of areas of modern bioscience and biomedical research. It can also be used for tracking macromolecule movement in living cells due to near infra-red emission, as well as work as a reporter for stable cell lines, therapeutic viral incorporation and replication experiments.

In addition, a researcher could potentially use this technology for replacing quantum dots (Q-dots) for monitoring vasculature during in vivo imaging studies. Quantum dots are nanocrystals with unique chemical properties that provide tight control over the spectral characteristics of the fluorophore. They are nanoscale-sized (2-50 nm) semiconductors that, when excited, emit fluorescence at a wavelength based on the size of the particle; smaller quantum dots emit higher energy than large quantum dots, and therefore the emitted light shifts from blue to red as the size of the nanocrystal increases. Because quantum dot size can be tightly controlled, there is greater specificity for distinct excitation and emission wavelengths than other fluorophores. While the use of quantum dots in biological applications is increasing, there are reports of cell toxicity in response to the breakdown of the particles and their use can be cost-prohibitive. Monomeric SFP could replace Q-dots on nanoparticles that monitor vasculature during in vivo imaging studies. Similarly, it offers a unique ability to be incorporated as a fusion to single chain variable fragments or in the construct of engineered antibodies. Currently, in vivo imaging of antibodies requires the chemical conjugation of dyes or Q-dots to antibodies to do this. Conjugation of these dyes can significantly decrease affinity to antigen as the reporter molecules may cross link in the space.

Besides being able to use the Sandercyanin in many of the applications where Green Fluorescent Proteins are currently used, one can also use it for detection of proteins (protein interaction in Fluorescence Resonance Energy Transfer—FRET). Specifically, the large energy difference in excitation may allow for a clearer signal if the Sandercyanin protein is used in combination with a Cy5 based dye.

Monomeric SFP also has improved quenching time, which will provide fluorescence with extra-long quenching time when compared to existing technologies.

Half-life is another important factor that influences the quality of the protein being used as well as brightness, in which monomeric SFP also stands out for being a stable protein with high brightness as compared to other fluorescent proteins.

Finally, monomeric SFP does not require cofactors to exhibit intrinsic fluorescence whereas other fluorescent proteins do require them.

Further, fluorophores in the far red and near infrared region (~650-850 nm) are useful for in vivo optical imaging, where the expression of monomeric SFP, either alone or tagged to another target protein, could be monitored in a live animal model (mouse, rat, zebrafish, etc.). An advantage to in vivo imaging is that complex tumor and/or normal tissue models can be developed and tested. For example, murine tumor models may behave very differently than cells cultured in vitro, as the animal model allows for the complex mix of normal tissue cells, tumor vascular supply and endothelial cells, supporting cells, along with the tumor cell being tested, to grow and behave much more like a "real" tumor would behave.

Spectral properties of monomeric SFP would allow for excitation of the agent in the short wavelength near UV/UV spectrum and emission in the NIR. Currently, there are no commercially available imaging agents, with the exception of toxic (cadmium containing) quantum dots. The current invention would allow for the spectral red shift only available with quantum dots to be used in vivo.

Further uses of the claimed inventions include using the protein for reporter stable cell lines or using it as a reporter for monitoring tumor growth. In some embodiments, monomeric SFP could take the place of GFP and/or luciferase as a reporter for therapeutic viral incorporation and replication experiments. The use of therapeutic viruses, such as conditionally replicative adenoviruses, has become a more desirable method for treating various cancers. Currently, these are studied in the laboratory in vitro and in vivo. To determine viral infectivity, GFP is often used as the reporter gene product. However, when translated in vivo this becomes difficult as GFP is not able to penetrate through tissue. Similar to the above, luciferase can be used, however, you are limited in the number of time points data can be collected by the requirement of the substrate luciferin to be injected into the animals. Monomeric SFP could be used as a reporter both in vitro and in vivo, limiting the number of "unnatural" gene products produced by therapeutic viral constructs (i.e., both GFP and luciferase) and would offer the ability for nearly continuous monitoring of viral infection via NIR imaging in host animals.

Additionally, Sandercyanin could be used as a direct replacement for GFP or similar molecules in confocal microscopy, flow cytometry, fluorescence microscopy, and other optical based spectroscopy methods. Again, the unique spectral properties would allow for Sandercyanin to be incorporated with other fluorophores without overlap of excitation/emission spectra, allowing for Sandercyanin to be visualized without interference by other fluorescent proteins. Sandercyanin would allow for a greater spectral range in confocal microscopy studies. For the above reason it could be used with other far-red dyes yet theoretically have little signal overlap as the excitation would be significantly far apart in the spectrum. Being monomeric, Sandercyanin could be used in fusion gene products, such as GFP, to monitor the subcellular localization of proteins.

Additionally, monomeric SFP may be used in fluorescence resonance transfer experiments. The large energy difference in excitation may allow for a clearer signal if this was used in pair with a Cy5 based dye.

Expression in cancer cell lines for grafting into mice. Monomeric SFP could be used as an alternative to GFP and Luciferase as a reporter to follow tumor size and/or response to treatment via in vivo optical imaging. This would be done by expressing monomeric SFP in desired cell lines via standard lentiviral methods to develop a stable transgenic line. This line can be sorted in vitro using flow cytometry directly using SFP as the reporter if needed prior to tumor initiation. Monomeric SFP could take the place of luciferase as the in vivo reporter gene. This would be less costly, as there would be no need for injections of a substrate (luciferin) and imaging would take less time as the NIR reporter could be directly imaged without additional substrates.

Sandercyanin would allow for a greater spectral range in confocal microscopy studies. For the above reason it could be used with other far-red dyes yet theoretically have little signal overlap as the excitation would be significantly far apart in the spectrum. Being monomeric, mSFP could be used in fusion gene products, such as GFP, to monitor the subcellular localization of proteins.

In the specification and in the claims, the terms "including" and "comprising" are open-ended terms and should be interpreted to mean "including, but not limited to. . . . " These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1—A Biliverdin-Inducible Near-Infrared Fluorescent Protein

Here, we report structure and spectral properties of a protein, Sandercyanin (isolated initially from the mucous of Canadian blue walleye), which binds a non-covalent ligand, has a large Stokes shift and emits in the near infra-red region. Sandercyanin fluorescent protein (SFP) belongs to the lipocalin family of proteins. SFP has one of the largest Stokes shift known to date with excitation/emission maxima of 375/675 nm respectively. The protein-ligand interaction was elucidated from the structure of Sandercyanin as determined by X-ray crystallography of protein purified from the fish and recombinant protein. The structure reveals presence of a non-covalent chromophore, Biliverdin IXα (BV), a tetrapyrrole with extended, conjugated-system. SFP monomers are 18.6 kDa. The monomers interact to form homotetramer upon addition of BV. When examined in walleye mucous cells and in solution, fluorescence from these proteins do not bleach even after several hours of excitation and emission. These data revealed spectral and structural properties that are advantageous for developing a ligand-inducible, highly photo-stable infra-red fluorescent protein.

Results

Figure 7A:
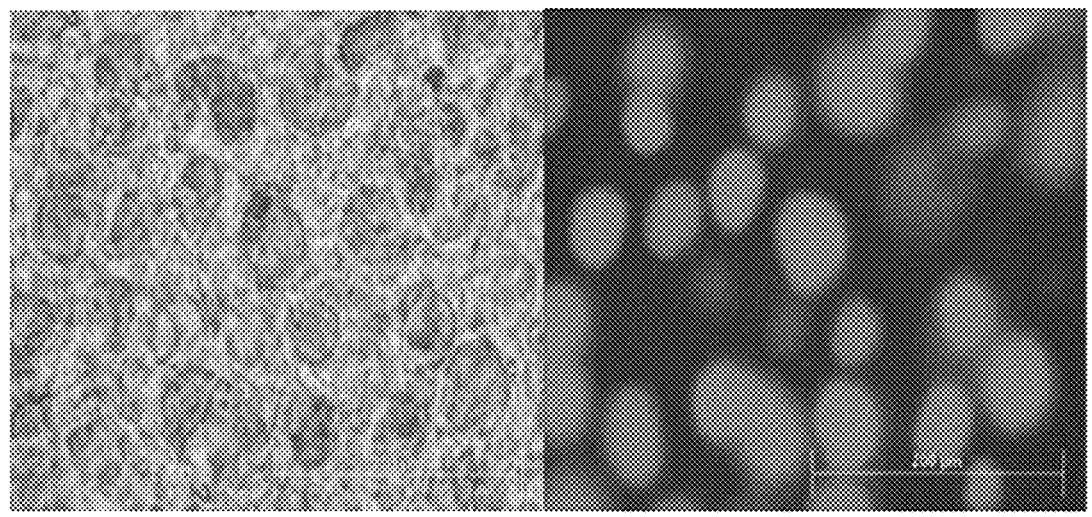
FIGS. 7A-7B presents characterization, cloning, and physical properties of SFP. (A) Mucous from Canadian Walleye (Sander Vitreous) appears blue under bright field and shows intense red fluorescence on excitation with DAPI blue laser. (B) Biliverdin (BV)-induced tetramerization in SFP. SFP (no biliverdin) 702, SFP+50 uM biliverdin 704, SFP+100 uM biliverdin 706, SFP+500 uM biliverdin 708.
Figure 7B:
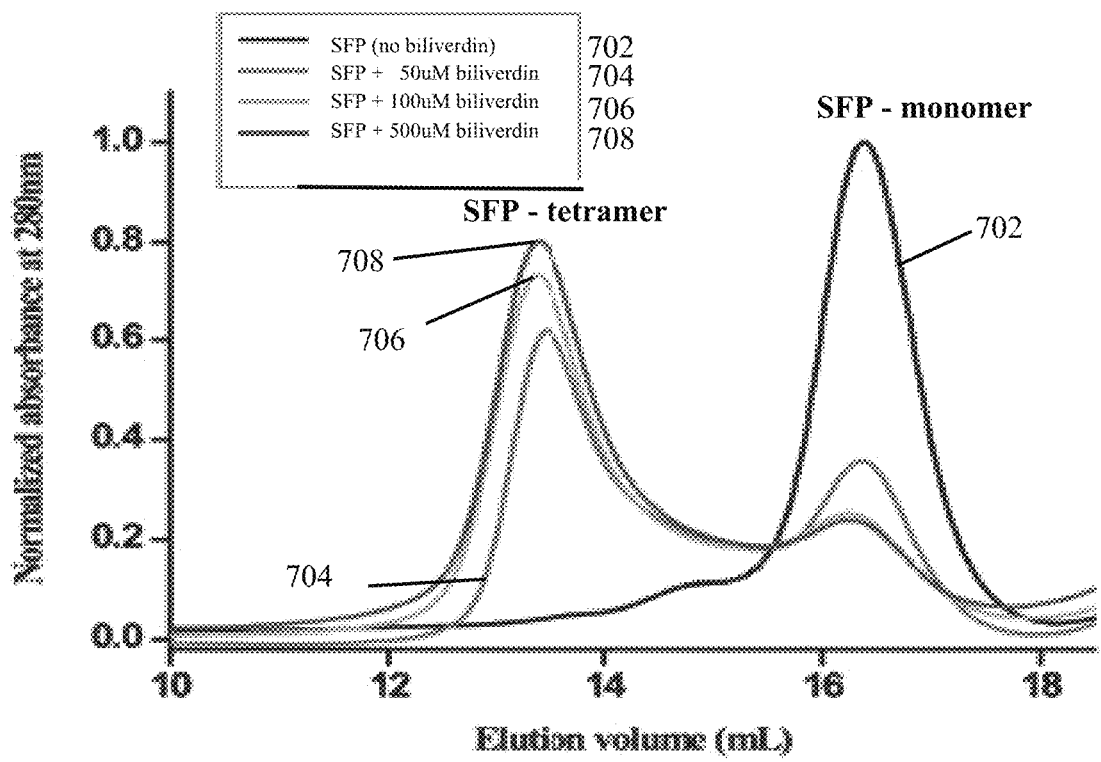

Characterization, cloning and expression of SFP: Sandercyanin is found in the mucosa of Canadian Blue walleye in the form of blue vesicles (1, 3). Recently, we discovered that these vesicles show bright red fluorescence (FIG. 7A) when excited with blue light. Although the fluorescence property of Sandercyanin was not reported previously, Chi Li et al. (1) had purified the native blue protein from the mucosa and reported the partial protein sequence of Sandercyanin which suggested that it belongs to lipocalin protein family (4, 5). Alignment with other proteins in the database show that Sandercyanin has close homology to lipocalins from two different fish, namely, apolipoprotein D (*Larimichthys crocea*) and an unannotated peptide (*Tetraodon nigroviridis*). We determined the full length gene sequence of SFP by partial assembly of whole genome of Bluewalleye based on mapping of known internal-peptides (1). The gene sequence, encoding for 170 amino acid residues was obtained and cloned for bacterial expression. Sandercyanin was expressed, denatured using chemical denaturant, refolded and purified from bacterial inclusion bodies as a functional protein with high purity and monodispersity for biochemical and structural studies. Preliminary circular dichroism studies show that Sandercyanin has a beta-barrel secondary structure and reveals conformation selection of BV due to induced chirality (32), with appearance of significant absorbance bands at 380 nm and 630 nm. We also observed that Sandercyanin predominantly exists as a small monomer protein in nature but quickly oligomerizes to a blue colored homotetramer (FIG. 7B) of 75 kDa in the presence of its chromophore, biliverdin (BV), which binds non-covalently to each monomer. On titration of apoSFP with increasing concentration of BV, the fraction of tetramer increases with ligand concentration. However, there was no dimer fraction in any intermediate concentration, suggesting that SFP dimer is a transient species and there exists equilibrium between monomer and tetramer forms. We further observed that oligomerization in SFP is reversed by exposure to UV (375 nm) and red light (630 nm), inferring that BV acts as a molecular switch that controls oligomerization of Sandercyanin, and could be reversed by light illumination.

Figure 8A:
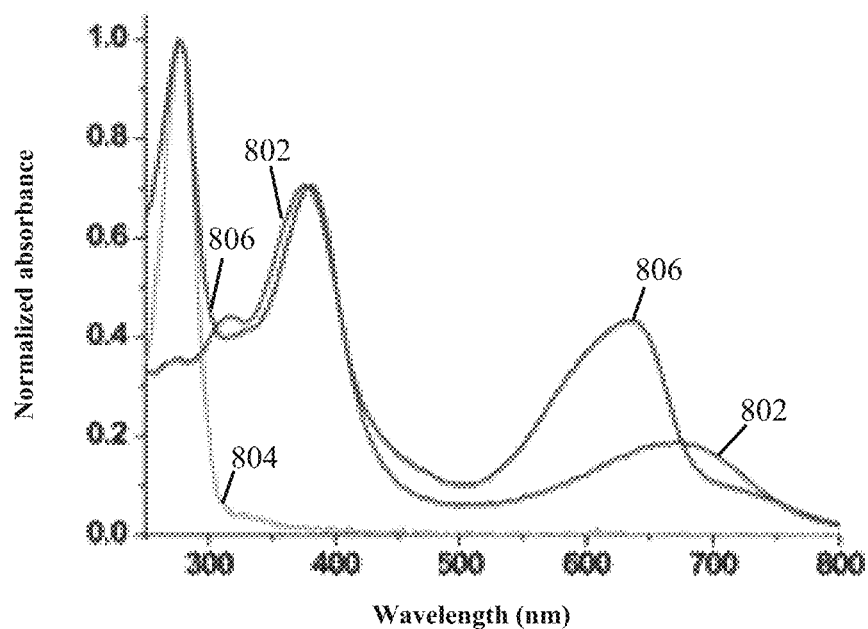
FIGS. 8A-8B demonstrate biliverdin (BV)-inducible near-infrared fluorescence of SFP and binding analysis. (A) Normalized absorption spectra of BV IXa (green 802), apo SFP (orange 804), holoSFP (blue 806). (B) Normalized fluorescence spectra of BV IXa (green 810 and orange 812) and holoSFP (blue 814 and red 816) on excitation at 375 nm and 630 nm respectively.
Figure 8B:
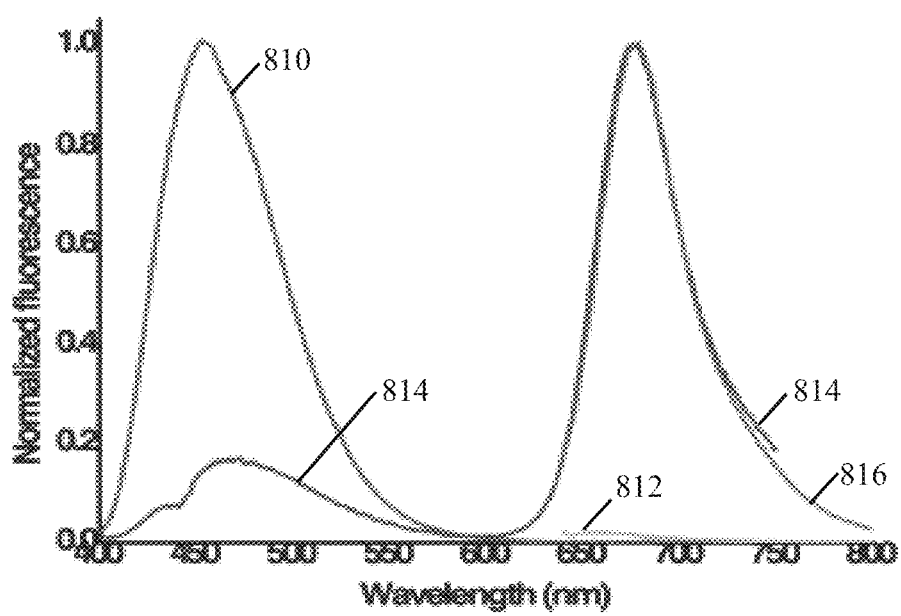
Figure 10A:
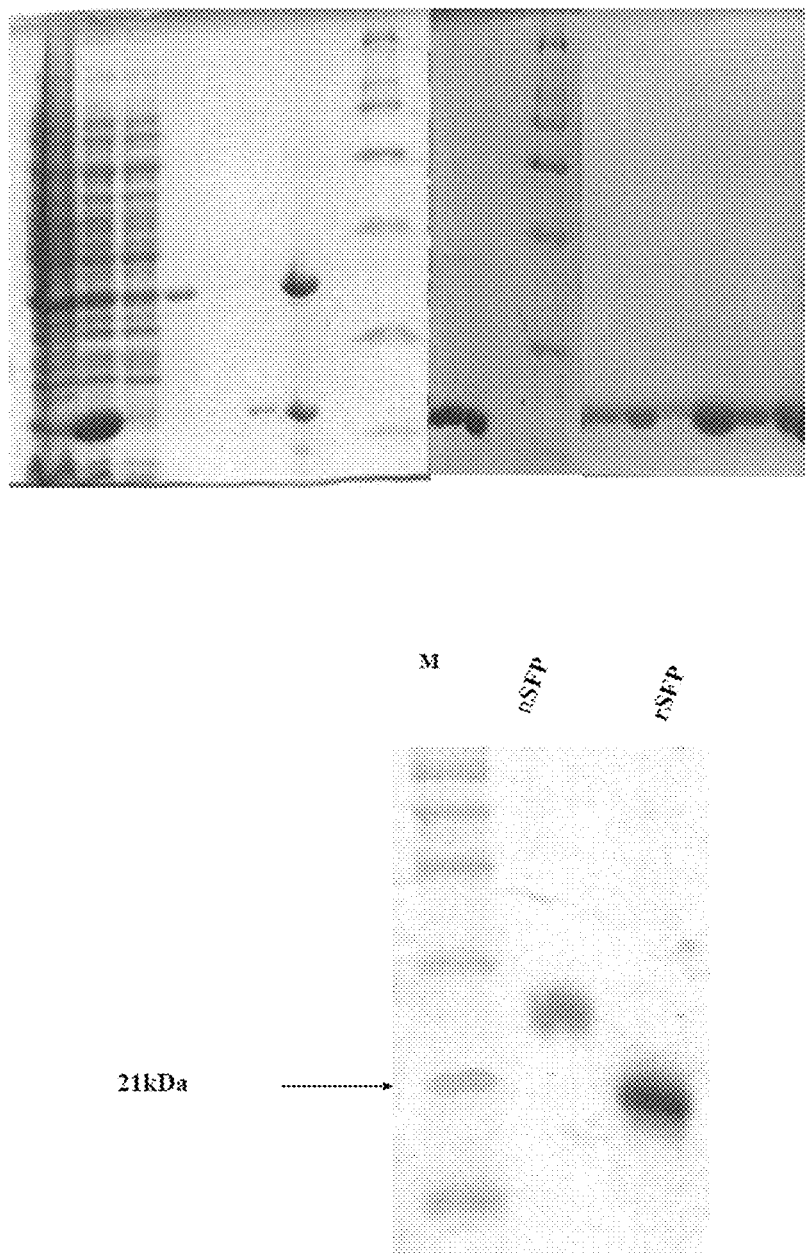
FIGS. 10A-10D show expression purification and physical properties of SFP.
Figure 10B:
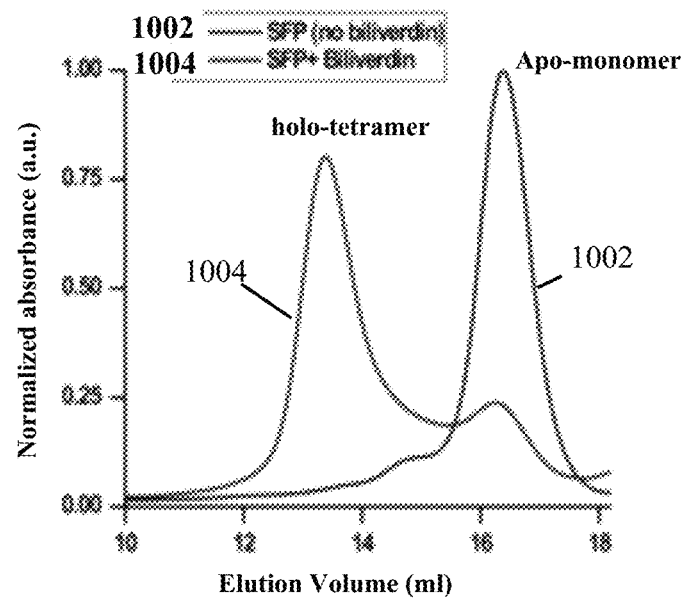
Figure 10C:
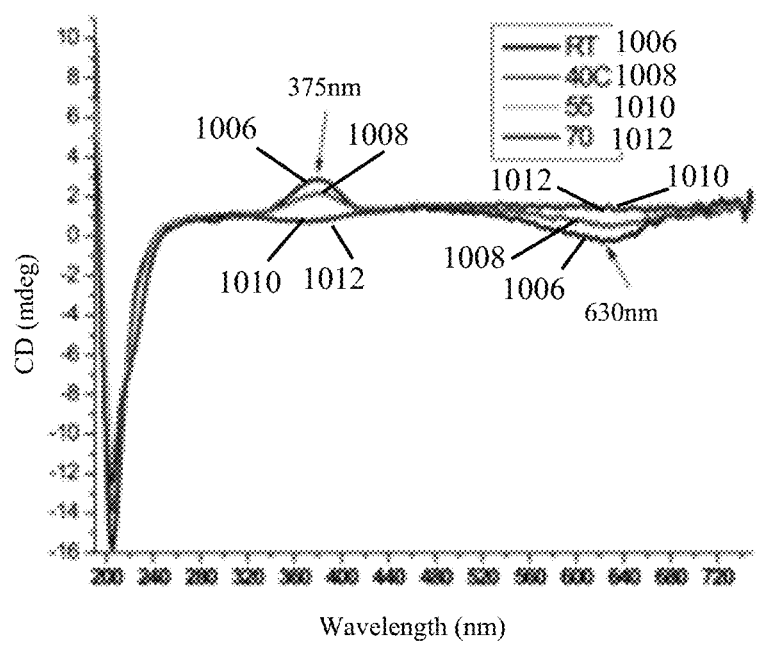
Figure 10D:
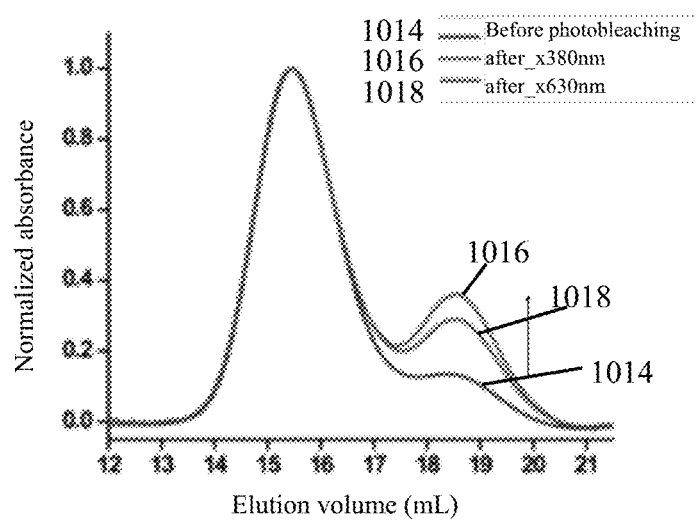
Figures 11A, 11B:
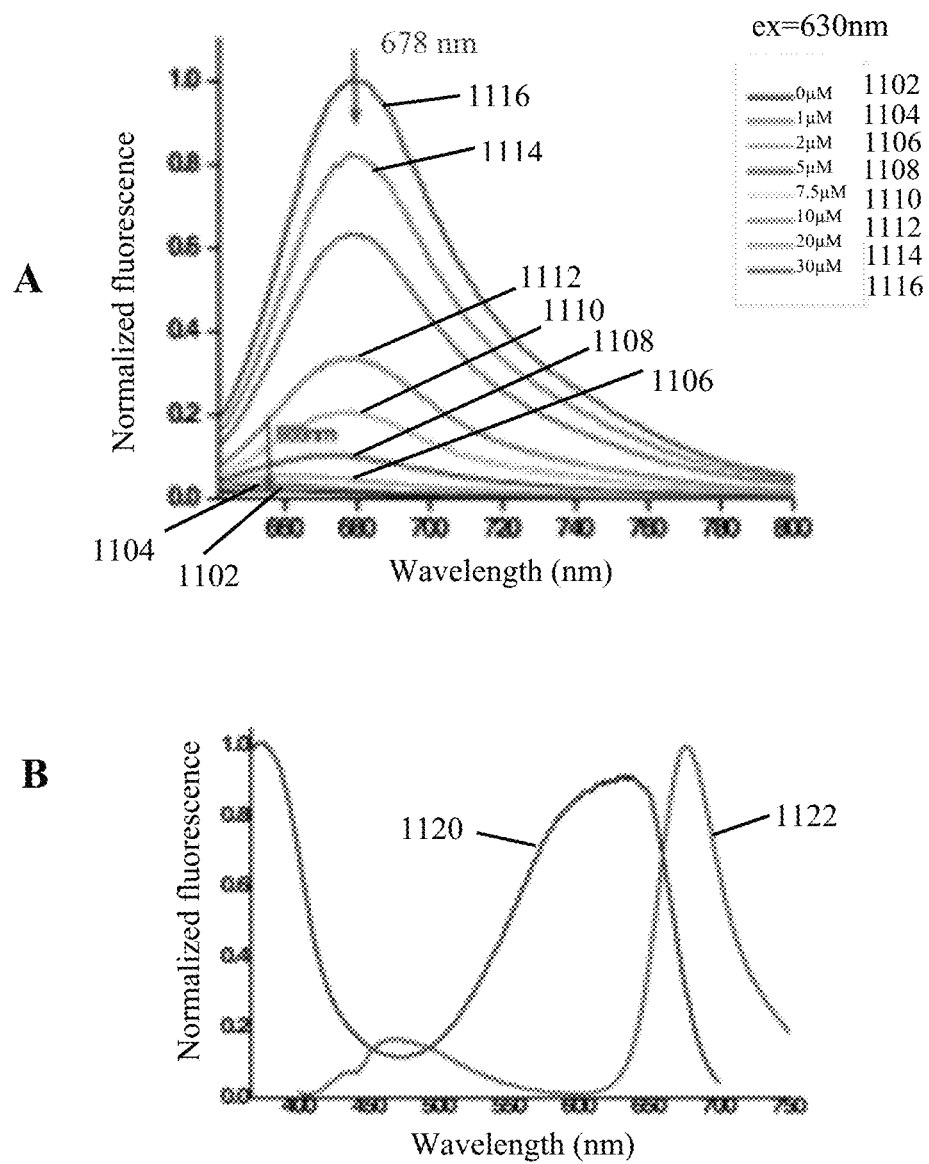
Figure 11C:
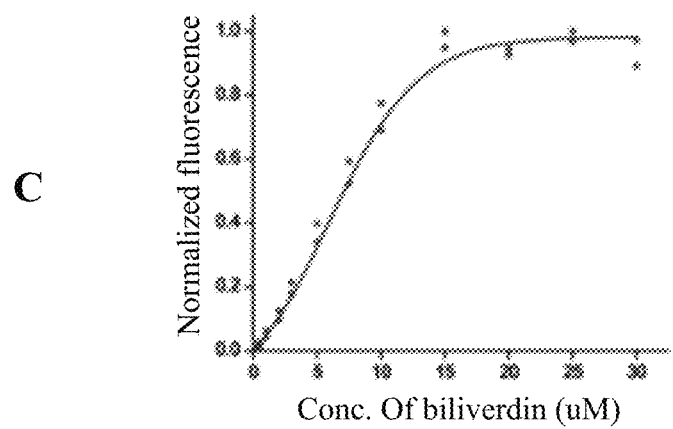
Figure 11D:
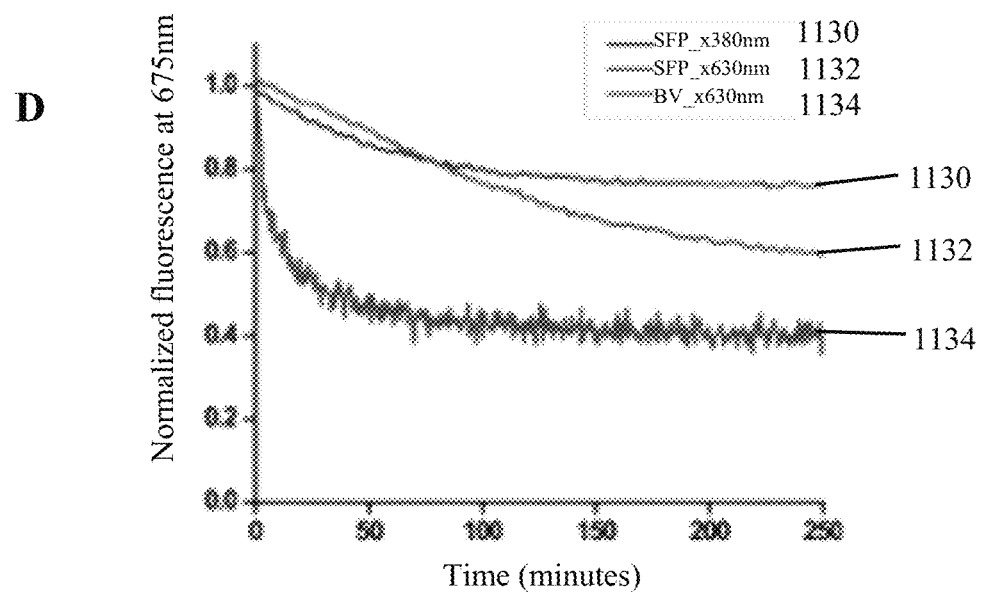
Figure 11E:
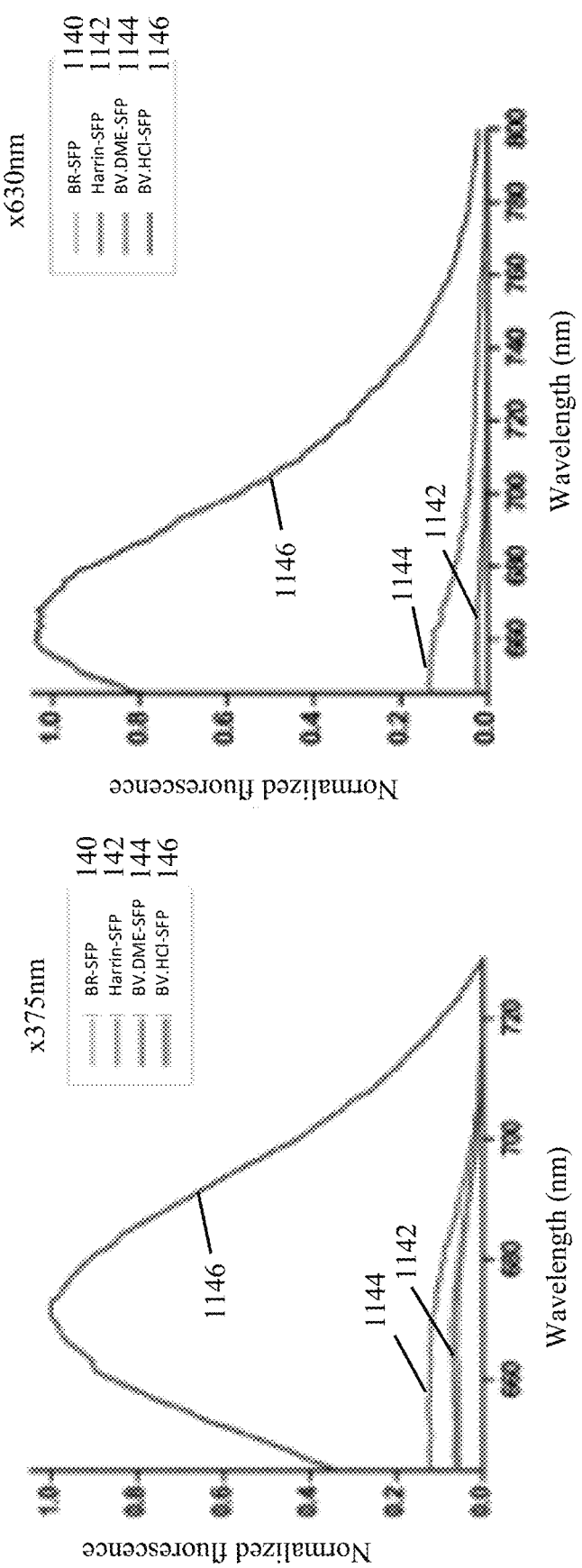
Figure 11F:
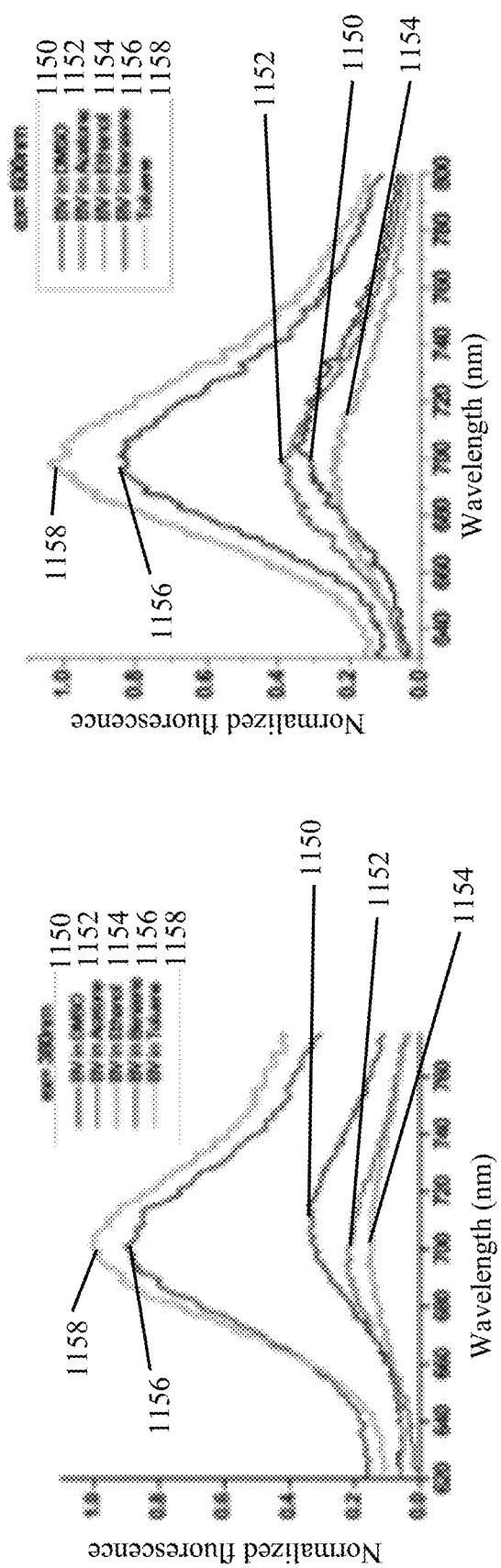
Figure 11H:
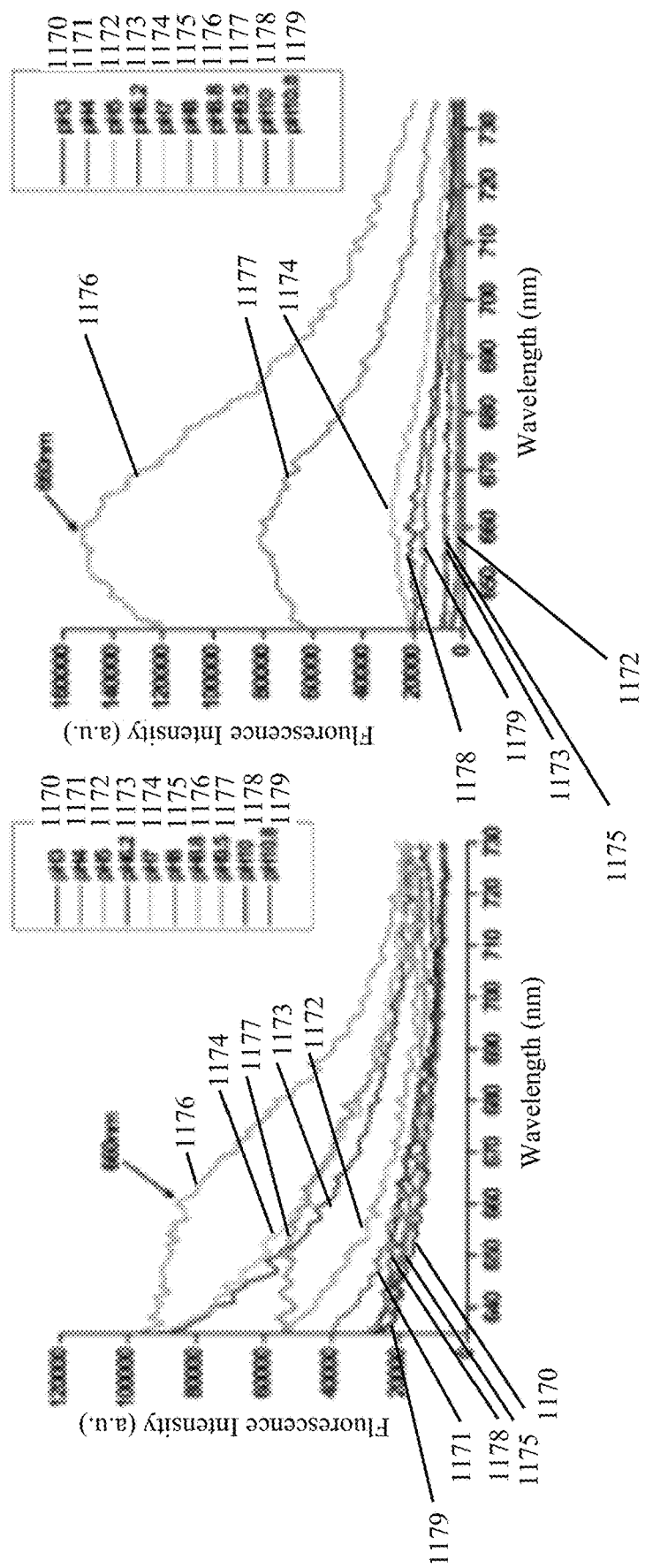
Figure 11I:
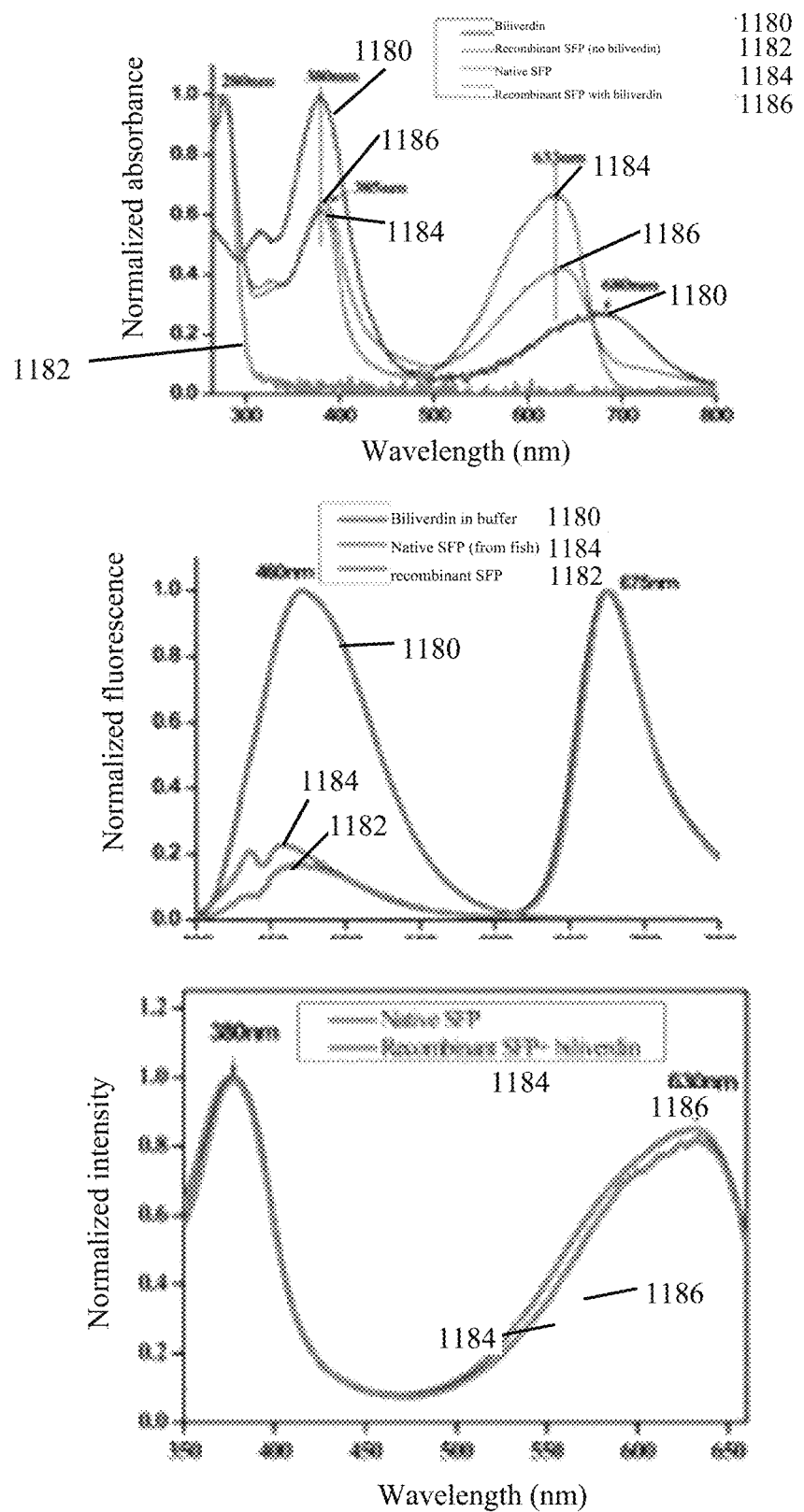
Figure 12A:
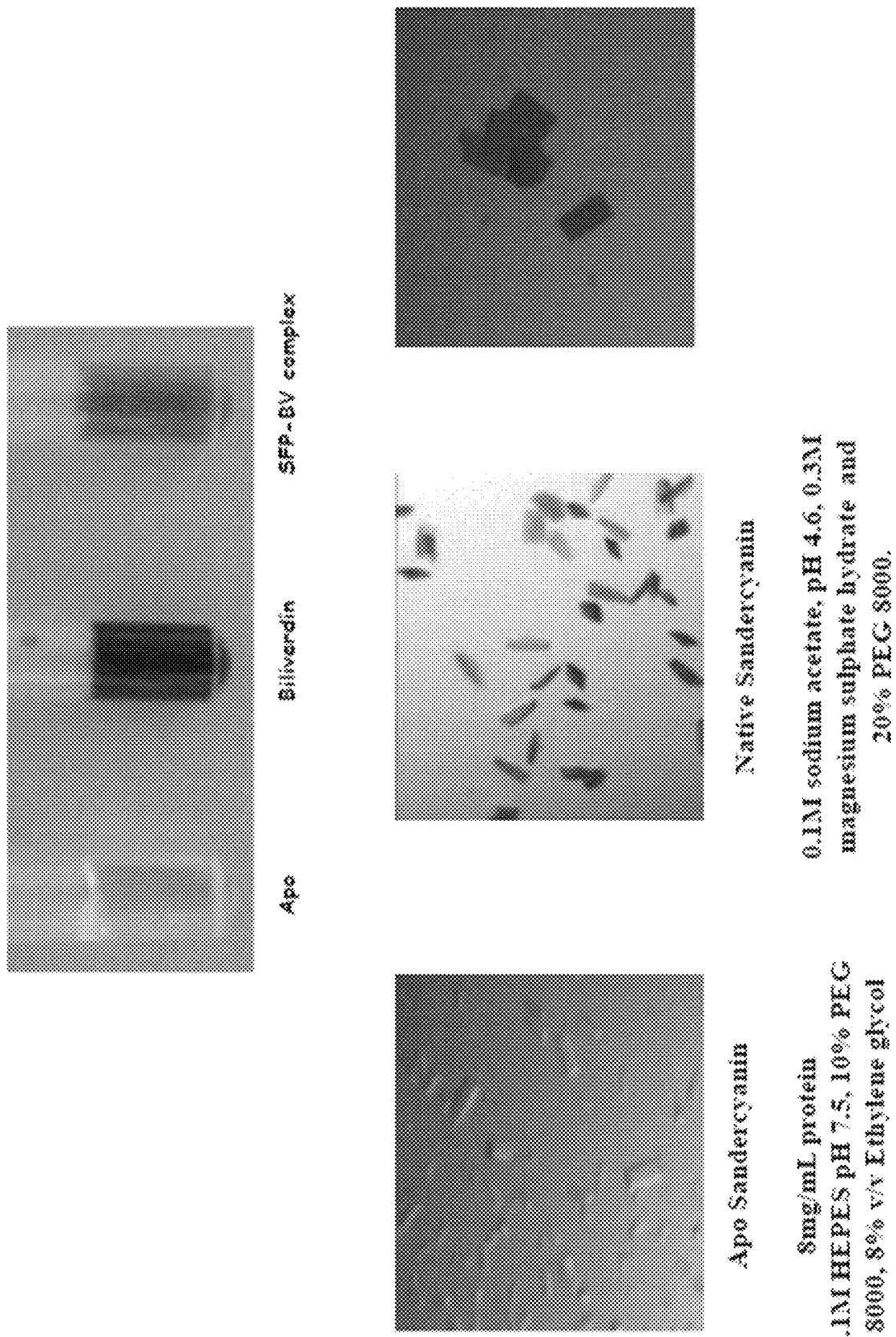
Figure 12D:
Figures 13A, 13B, 13C:
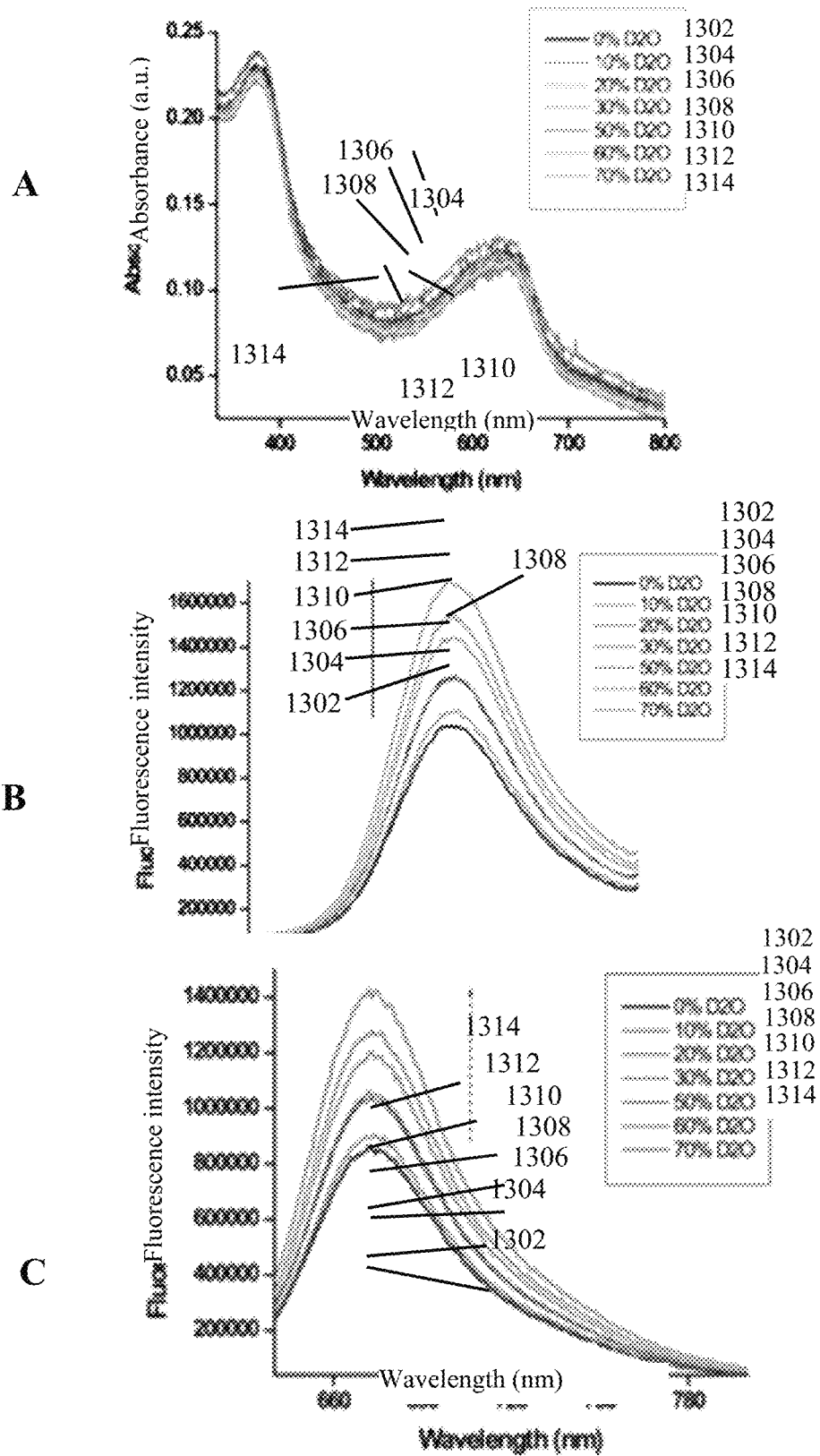
FIGS. 13A-13C shows absorbance (A) and emission spectra of Sandercyanin monitored on excitation at (B) 375 nm and (C) 630 nm at different D2O concentrations, showing influence of proton transfer on the fluorescence properties of SFP. Labels are as follows: 0% D20 1302, 10% D2O 1304, 20% D2O 1306, 30% D2O 1308, 50% D2O 1310, 60% D2O 1312, 70% D20 1314.

Near-infrared fluorescence properties of Sandercyanin fluorescent protein (SFP): Spectroscopic properties of purified SFP shows absorbance maxima at 280, 375, and 630 nm at physiological pH (FIG. 8A) and a strong near infrared fluorescence maxima at 675 nm, when excited at 375 nm and 630 nm (FIG. 8B). Addition of the biliverdin to apo-protein results in red-shift in the fluorescence of Sandercyanin to near infra-red (NIR) region. Molar extinction coefficient of holoSFP measured in phosphate buffer of pH 7.4 at 375 nm and 630 nm are 21,000 $M^{-1}$ $cm^{-1}$ and 13,500 $M^{-1}$ $cm^{-1}$ respectively and quantum yield is determined to be 0.016. Further, fluorescence spectra is widely spread into the infra-red region with minimal overlap with the excitation spectra. We examined the affinity of apoSFP towards BV using fluorescence and determined $K_d$ of 6 µM. Photo-stability studies show that fluorescence of Sandercyanin does not bleach significantly on overnight exposure with UV or red light. Further, we observed that BV free form bleaches faster than its complex with Sandercyanin.

To examine the specificity of Sandercyanin to bilverdin IXa, we tested other BV-like tetrapyrrol compounds: hemin, bilirubin, and esterified BV derivatives. Sandercyanin does not show binding and fluorescence with BV-like compounds, inferring specificity of apoSFP to BV IXa.

We performed experiments with free biliverdin in different solvents conditions, to understand the molecular basis of the observed fluorescent properties of Sandercyanin-BV complex. Biliverdin shows enhanced far red fluorescence as the hydrophobicity of the medium was increased. A similar trend was observed on increasing the viscosity of medium with increased polyethylene glycol and changing the pH of medium to pH 8.8-9.5. Our data also show that bacterial expressed holoSFP has the similar spectral properties with the protein purified from Blue Walleye.

Crystal structure of apo and holo SFP reveals molecular basis of biliverdin binding: In order to correlate the biochemical and photo-physical properties with the atomic structure, we crystallized native and recombinant proteins to understand the molecular basis of BV-binding to SFP. All the crystals were obtained in different conditions of buffer, salt and precipitant concentration. Firstly, we determined a structure of native Sandercyanin using multiple anomalous diffraction (MAD) (33, 34) as there was no structural model available. Native SFP crystals were soaked in $AuCl_3$ and data was collected at the Au edge. Further, structures of recombinant holo and apo forms of Sandercyanin were determined at 1.8 Å and 2.6 Å, respectively, using molecular replacement with native SFP as template structure for phase determination. Crystal structure shows that SFP is a tightly packed tetramer (FIG. 9A), with each monomer binding non-covalently to one biliverdin (BV) molecule. SFP structure consists of 8 anti-parallel β-strands forming a barrel, an external α-helix and capped by a long loop closing the barrel (FIG. 9B, i and ii), similar to many lipocalins (4, 5). The barrel encloses a hydrophobic environment around the ligand (FIG. 9C). Further, there are two intramolecular disulphide bonds between cysteine at the N- and C-terminal, which hold the β-strands in the three-dimensional. These cysteine, forming disulphide bonds, are highly conserved in lipocalins and important for structural stability of protein. We also determined that SFP is glycosylated at position Asn 83, which may be essential for stability during folding of secreted proteins in eukaryotes (35, 36). An insight into the crystal structure shows that BV is accommodated at the centre of the barrel and assumes a ZZZssa configuration (FIG. 9D) (37-38). The vinyl groups of ring A and D are buried deep in the cavity, while the propionate side-chains of ring B and C are located near the entrance of the barrel. The ligand is mostly planar and stabilized by steric interactions with aromatic amino acids (FIG. 9E), where Phe 55 and His 108 stacks with BV pyrrole rings B and C respectively. Mutation of Phe 55 to alanine abolished BV binding, suggesting that ligand is stabilized by aromatic stacking interaction with Phe 55. D-ring rotation in SFP, which have been extensively studied in bacteriophytochemores (38-41), is hindered by Tyr 116 and Tyr 142. We also observed interaction of propionate groups with Lys 57 and Lys 87 which may play significant role in stabilizing the chromophore in the binding pocket. BV also forms water-mediated hydrogen bonds with His108, Asn 77 and Tyr 65 through well-ordered water molecules. Proton transfer mechanisms and hydrogen bonding (42, 43) have shown to have significant effects on the fluorescent properties of most fluorescent proteins known so far. These data demonstrate that steric interactions due to aromatic residues and ionic interactions, with the help of water-mediated hydrogen bonding, likely contribute to the binding, stabilization, and fluorescence properties of SFP.

To further investigate on the structural changes at the ligand-binding pocket, we determined a structure of apoSFP. Although apoSFP exists as a monomer in solution, it appears as a tetramer in the crystal structure as a result of lattice contacts. The overall structure is highly similar to holo protein tetramer, without any significant changes on the oligomerization interface. However, in the absence of biliverdin, structure of apoSFP density for the enclosing loop spanning across Lys54-Lys57 is missing, supporting a conclusion that loss of stacking between Phe55 and B-ring of biliverdin makes the loop highly dynamic and unstructured. Moreover, aromatic residues in the ligand-binding pocket show minor changes near the D-ring and B-ring propionate of biliverdin, however they interact with their neighboring residues in the protein which stabilizes them in absence of the ligand.

On comparing the crystal structures of native Sandercyanin purified from Blue Walleye to recombinantly expressed holo-protein, we observed conformation changes in the N-terminal residues Met20 and Phe21. In native SFP, Ser20 is positioned towards the D-ring, while Met20 in recombinant protein is directed outwards, flipping the aromatic ring of Phe21 towards the ligand. However, conformation of BV remains the same and there are no significant changes in the overall secondary structure and position of the residues involved in glycosylation. These results suggest that binding of BV and fluorescent properties of SFP are minimally perturbed by changes in the N-terminus and/or de-glycosylation. We also observed in the crystal structure that in one dimer interface, BV bound to one monomer interacts with the residues of a neighboring subunit. Ser138 and Leu135 backbone forms water-mediate H-bond with C-ring carboxylate and D-ring carbonyl group respectively. Moreover, vinyl group of D-ring coordinates with the hydrophobic residues of a neighboring subunit. These interaction could possibly favor BV-induced oligomerization in SFP. However, interaction between BV is not possible due to large spatial distance. The other interface presents protein-protein interaction. This is also stabilized by H-bonding via solvent molecules and hydrophobic interaction between amino acids. Overall, both interfaces present a two-fold symmetrical arrangement of residues.

Discussion

In this work, we describe the biochemical and photo-physical properties of a newly discovered protein, Sandercyanin. Sandercyanin fluorescent protein (SFP) exists as homo tetramer comprising four monomer subunits, each 18.6 kDa. This is, by far, the smallest far-red fluorescent protein reported which has ligand-inducible fluorescence. Secondly, SFP has one of the largest Stokes shift which gets excited by blue light of 375 nm and shows far-red fluorescence with maxima at 67 nm. Further, we found that biliverdin is the natural ligand which binds specifically and non-covalently to SFP. Our solution state experiments also reveal that oligomerization of SFP is promoted on addition of biliverdin.

Our work also presents the first recombinant expression of newly synthesized gene for SFP and efficiency of protein refolding methods to form functional proteins with disulphide bonds from completely denatured protein. On comparing the functional and structural properties of native and recombinant SFP, we found no significant differences, thus, hypothesizing that glycosylation in native protein has minimal effect on the binding of biliverdin and spectral properties of Sandercyanin.

We studied fluorescent properties of free biliverdin in different solvents, and solved the high resolution atomic structures of native and recombinant SFP. Biliverdin showed enhanced red-fluorescence with increased hydrophobicity and viscosity of its surrounding media. We also observed that biliverdin fluorescence is pH-dependent. Our high resolution crystal structures of Sandercyanin also reveal a lipocalin fold with highly hydrophobic pocket in the centre of the barrel and presence of stacking interaction and water mediated H-bonding between protein and its chromophore. Combining our biliverdin experiments with functional and structural data of SFP, we hypothesize that hydrophobicity, rigidity and H-bonding network in the ligand-binding pocket have important roles for BV to lose it excess energy on excitation and generate near-infrared fluorescence with a large Stokes shift.

Many biliverdin-binding lipocalins have been identified that bind to the biliverdin IX-gamma isoform of the chromophore and impart blue color. SFP is the first lipocalin to be identified as having biliverdin-inducible fluorescence properties. Moreover, the structures of these proteins were solved from the natural sources, with no apo protein structure available to elucidate changes during chromophore-binding. On comparison of the structure of SFP with those of previously reported Insecticyanin (PDB 1BBP) (44) and bilin-binding protein (PDB 1Z24) from *Pieris brassicae* (45), we found similar interactions between protein and its chromophore, revealing that stacking interaction, hydrophobicity of environment and H-bonding play major role in biliverdin binding.

Further, Sandercyanin differs from previously reported bilin-binding phytochromes (46, 47) with respect to its binding to its chromatophore. In phytochromes, one of the pyrrole rings of the chromophore associates covalently with a cysteine of the apo-protein (37, 38). Sandercyanin structures neither reveal presence of any cysteine within close-proximity to biliverdin nor show any other covalent association. Moreover, bacteriophytochromes are well-studied photo-switches; their mechanism of photo-conversion and structures of biliverdin in red (Pr) to far-red (Pfr) absorption (38-40) have been revealed by time-resolved (39, 48) and pump-probes methods (49). It would be interesting to study whether Sandercyanin has photo-switching properties similar to bacteriophytochromes. It has been proposed that proton-transfer and hydrogen-bond interaction have significant role in determining their fluorescence quantum yield (37). Excited state proton transfer (ESPT) in GFP (42, 43) and its variant proteins have been known for decades, which are key players in red-shifting their fluorescence (24, 25, 50). To understand if proton transfer has any effect on the fluorescent properties of SFP, we performed experiments with increasing concentrations of D in place of H in the purified protein. Our experiments showed increased fluorescence intensity of SFP with increasing concentrations of $D_2O$ (or more of the H's replaced by D's in the protein) with no changes in the absorbance, suggesting that excited state proton transfer mechanisms may play crucial role in affecting fluorescence properties of the protein.

A large stokes shift in a fluorescent protein is influenced by the immediate environment of its chromophore. Previous reports on red fluorescent proteins (24, 25) suggest that H-bonding and pi-pi stacking interaction play significant roles in shifting fluorescence spectra of protein. For instance, mCherry, mKate, and DsRed red fluorescent proteins have been engineered for longer emission wavelength (51) by perturbing the interactions between the chromophore and protein. Hence, we hypothesize that the large Stokes shift of SFP is a combined effect of interaction of biliverdin with its neighboring residues in the binding pocket.

Methods and Materials for Example 1

Native SFP was extracted and purified from the mucus of Blue Walleye from Northwest Ontario by various chromatographic methods as described previously (Chi Li et al). A putative amino acid sequence of SFP was determined from crystal structure of the native protein, confirmed and corrected after whole genome sequencing of Blue Walleye. Genome sequence revealed the presence of a secretion signal sequence which was not observed in the native crystal structure. The SFP gene (without the signal peptide) was synthesized from GeneScript (Invitrogen) and cloned into pET21a bacterial expression vector between NdeI and HindIII cloning sites. For recombinant protein expression, BL21*(De3) cells are transformed with the SFP-pET21a and over-expressed. Cells were grown in LB-medium to an $OD_{600}$ of 0.6-0.7 and induced with 0.2 mM isopropyl-thiogalactoside (IPTG) for 20 h at 20° C. The protein was purified from the inclusion bodies (IBs) by chemical denaturation and subsequent refolding by slow dialysis. The cell-pellet was re-suspended in 50 mL of IB-wash buffer (20 mM Tris.HCl, pH 7.5, 10 mM EDTA and 1% TritonX) and sonicated using macro-probe (Fisher Scientific) for 3 cycles of 3 min each with 10 s on and 30 off pulses at 50% amplitude. The cell-lysate was centrifuged for 30 min at 13,000 r.p.m in Avanti J-26 XP centrifuge and JA17 rotor from Beckmann Coulter to obtain pure IBs (white residue). This was re-suspended in a solution containing 5M Guanidine.HCl, 50 mM CAPS, 0.5 mM phenylmethylsulfony fluoride (PMSF) and 1 mM DTT, pH 7.5 and incubated at room temperature to solubilize the IBs. The denatured protein from IBs was refolded by rapid dilution method; 20 mg of solubilized IBs were rapidly diluted in 25 mL of buffer containing 1.1M Guanidine.HCl, 50 mM Tris-base, pH 7.5, 50 mM NaCl, 0.88 mM KCl, 10% glycerol, redox containing 5 mM/1 mM of reduced/oxidized L-cysteine and 1 uM Biliverdin IXa hydrochloride (Santa Cruz Biotechnology, USA). This was then dialyzed using 3.5 kDa MWCO tubing (Fisher Scientific) overnight in 2 L of the same buffer without guanidine.HCl. The refolded protein was concentrated using 3 kDa Centricon (Millipore) and passed through a Superdex 200 analytical size exclusion column (GE Healthcare). Blue-colored protein fractions, corresponding to size of 75 kDa were collected, concentrated to 8 mg/mL and set up for crystallization. Apo-SFP was purified using the same methodology in buffer solutions without biliverdin and collected as monomeric protein by size-exclusion chromatography.

All experiments were performed with purified SFP samples (apo and holo forms) at pH 7.5 and room temperature. UV-Visible absorbance spectra of native and recombinant SFP were recorded from 800 to 200 nm with ultraspec 2100 pro spectrophotometer from Amersham Biosciences. CD spectra were measured on JASCO J-815 Spectropolarimeter. Steady state fluorescence, excitation, binding and photobleaching studies were monitored on Horiba Jobin Yvon Fluoromax-4 fluorimeter. Data analysis were done using Origin6 and Origin8 software. Hydrogen was exchanged with Deuterium by increasing concentrations of D2O to a standard protein concentration. Deuteriated proteins were prepared in the same buffer, incubated for 15 minutes, and monitored for spectral properties.

Crystallization of SFP (native and recombinant) were carried out at 4° C. in hanging drops vapor diffusion method using mosquito high-throughput crystallization system from TPP life sciences. All protein crystals were obtained in different conditions and flash frozen after soaking in 10% ethylene glycol as cryo-protectant. MAD datasets for native SFP crystal data were collected from crystals soaked in Au. The structure was solved using the SOLVE-RESOLVE package (Terwilliger, T. C. and J. Berendzen. (1999) "Automated MAD and MIR structure solution". Acta Crystallographica D55, 849-861). Recombinant apo- and holo-SFP datasets were collected at ID-23 and BM14 respectively in European Synchrotron Radiation Facility (ESRF, Grenoble, France). All images were indexed, integrated and scaled using HKL2000 and iMosflm. Molecular replacement for recombinant protein were performed using native SFP structure as template model and refined with PHENIX. 2Fo-Fc map showed presence of positive density indicating presence of ligand in the core of each monomer subunit. BV IXα was searched in PHENIX library and fitted into the density. Model building was done with Coot and all structural illustrations were generated with PyMol. All parameters of data collection and refinement statistics are summarized in Table 1.

TABLE 1

Data collection and refinement statistics

| Crystal | Native SFP (nSFP) with BV | Recombinant Apo-SFP (aSFP) | Recombinant SFP (rSFP) with BV |
|---|---|---|---|
| Data Collection | | | |
| Source | | BM14, Grenoble | BM14, Grenoble |
| Resolution range (A°) | 29.36-2.4 (1.968-1.9) | 53.4-2.7 (2.797-2.7) | 35.99-1.849 (1.915-1.849) |
| Space group | $P4_12_12$ | $P6_322$ | $P6_322$ |
| Cell dimensions | | | |
| Unit cell | 93.51 93.51 246.96 | 158.764 158.764 84.795 | 159.266 159.266 84.157 |
| Total reflections | | | |
| Unique reflections | 82481 (8223) | 17810 (1741) | 53181 (5194) |
| Multiplicity | | | |
| Completeness (%) | 94.73 (96.49) | 99.98 (99.94) | 98.47 (97.47) |
| Mean I/sigma (I) | 4.84 (2.77) | 31.48 (7.81) | 15.48 (1.90) |
| Wilson B-factor | 28.50 | 44.97 | 26.42 |
| R-sym | | | |
| R-factor | 0.2198 (0.4078) | 0.1896 (0.2259) | 0.1904 (0.2861) |
| R-free | 0.2762 (0.4155) | 0.2460 (0.2532) | 0.2125 (0.3044) |
| Number of atoms | 5581 | 2639 | 3107 |
| macromolecules | 5107 | 2556 | 2594 |
| ligands | 228 | | 106 |
| Water | 246 | 83 | 313 |
| Protein residues | 672 | 334 | 338 |
| RMS (bonds) | 0.007 | 0.010 | 0.019 |
| RMS (angles) | 1.20 | 1.19 | 1.56 |
| Ramachandran favored (%) | 97 | 96 | 98 |
| Ramachandran outliers (%) | 0 | 0 | 0 |
| Clashscore | 6.90 | 7.15 | 6.78 |
| Average B-factor | 39.90 | 25.40 | 25.20 |
| macromolecules | 39.60 | 25.50 | 24.10 |
| solvent | 42.20 | 21.60 | 34.50 |

* Statistics for the highest-resolution shell are shown in parentheses.

Example 1 References

1. Yu, C. L., Ferraro, D., Ramaswamy, S., Schmitz, M. H., Schaefer, W. F., & Gibson, D. T. (2008). Purification and properties of Sandercyanin, a blue protein secreted in the mucus of blue forms of walleye, Sander vitreus. Environmental Biology of Fishes, 82(1), 51-58.
2. Scott, W. B., and Crossman, E. J. 1973. Freshwater fishes of Canada. Bull. Fish. Res. Board Can. No. 184.
3. Schaefer, W. F., Schmitz, M. H., Blazer, V. S., Ehlinger, T. J., & Berges, J. A. (2015). Localization and seasonal variation of blue pigment (Sandercyanin) in walleye (Sander vitreus), 289 (October 2014), 281-289.
4. Flower, D. R., North, A. C. T., & Sansom, C. E. (2000). The lipocalin protein family: Structural and sequence overview. Biochimica et Biophysica Acta—Protein Structure and Molecular Enzymology.
5. Flower, D. R. (1996). The lipocalin protein family: structure and function. The Biochemical Journal, 318 (Pt 1, 1-14).
6. Chudakov, D. M., Matz, M. V, Lukyanov, S., & Lukyanov, K. A. (2010). Fluorescent proteins and their applications in imaging living cells and tissues. Physiological Reviews, 90(3), 1103-1163.
7. Day, R. N., & Davidson, M. W. (2009). The fluorescent protein palette: tools for cellular imaging. Chemical Society Reviews, 38(10), 2887-2921.
8. Shaner, N. C., Patterson, G. H., & Davidson, M. W. (2007). Advances in fluorescent protein technology. Journal of Cell Science, 120(Pt 24), 4247-4260.
9. Shcherbo, D., Murphy, C. S., Ermakova, G. V, Solovieva, E. A., Chepurnykh, T. V, Shcheglov, A. S., Chudakov, D. M. (2009). Far-red fluorescent tags for protein imaging in living tissues. The Biochemical Journal, 418(3), 567-574.
10. Stadler, C., Rexhepaj, E., Singan, V. R., Murphy, R. F., Pepperkok, R., Uhlén, M., . . . Lundberg, E. (2013). Immunofluorescence and fluorescent-protein tagging show high correlation for protein localization in mammalian cells. Nature Methods, 10(4), 315-23.
11. Hu, C.-D., Grinberg, A. V, & Kerppola, T. K. (2005). Visualization of protein interactions in living cells using bimolecular fluorescence complementation (BiFC) analysis. Current Protocols in Protein Science/Editorial Board, John E. Coligan [et Al.], Chapter 19, Unit 19.10.
12. Cabantous, S., & Waldo, G. S. (2006). In vivo and in vitro protein solubility assays using split GFP. Nature Methods, 3(10), 845-854.
13. Chakraborty, C., Saha, G., Sarkar, B., Pal, S., Chatterjee, T. K., & Sadhu, a K. (2006). Caspase-3 induced apoptosis in transgenic zebrafish. Biotechnology Letters, 28(3), 189-96.
14. Chalfie, M., Tu, Y., Euskirchen, G., Ward, W. W., & Prasher, D. C. (1994). Green fluorescent protein as a marker for gene expression. Science, 263 (5148), 802-805.
15. Wu, B., Piatkevich, K. D., Lionnet, T., Singer, R. H., & Verkhusha, V. V. (2011). Modern fluorescent proteins and imaging technologies to study gene expression, nuclear localization, and dynamics. Current Opinion in Cell Biology, 23(3), 310-317.
16. Chen, T.-W., Wardill, T. J., Sun, Y., Pulver, S. R., Renninger, S. L., Baohan, A., . . . Kim, D. S. (2013). Ultrasensitive fluorescent proteins for imaging neuronal activity. Nature, 499(7458), 295-300.
17. Perron, A., Mutoh, H., Launey, T., & Knöpfel, T. (2009). Red-Shifted Voltage-Sensitive Fluorescent Proteins. Chemistry and Biology, 16(12), 1268-1277.
18. Mérian, J., Gravier, J., Navarro, F., & Texier, I. (2012). Fluorescent nanoprobes dedicated to in vivo imaging: From preclinical validations to clinical translation. Molecules, 17(5), 5564-5591.
19. He, X., Gao, J., Gambhir, S. S., & Cheng, Z. (2010). Near-infrared fluorescent nanoprobes for cancer molecular imaging: Status and challenges. Trends in Molecular Medicine.

20. Progatzky, F., Dallman, M. J., & Lo Celso, C. (2013). From seeing to believing: labelling strategies for in vivo cell-tracking experiments. Interface Focus, 3(3), 20130001.
21. Tsien, R. Y. (1998). The green fluorescent protein. Annual Review of Biochemistry, 67, 509-544. Wiehler, J., Von Hummel, J., & Steipe, B. (2001).
22. Müller-Taubenberger, A., & Anderson, K. I. (2007). Recent advances using green and red fluorescent protein variants. Applied Microbiology and Biotechnology.
23. Verkhusha, V. V, & Lukyanov, K. A. (2004). The molecular properties and applications of Anthozoa fluorescent proteins and chromoproteins. Nature Biotechnology, 22(3), 289-296.
24. Wiehler, J., Von Hummel, J., & Steipe, B. (2001). Mutants of Discosoma red fluorescent protein with a GFP-like chromophore. FEBS Letters, 487(3), 384-389.
25. Subach, F. V, Piatkevich, K. D., & Verkhusha, V. V. (2011). Directed molecular evolution to design advanced red fluorescent proteins. Nature Methods, 8(12), 1019-1026.
26. Shu, X., Royant, A., Lin, M. Z., Aguilera, T. A., Lev-Ram, V., Steinbach, P. A., & Tsien, R. Y. (2009). Mammalian expression of infrared fluorescent proteins engineered from a bacterial phytochrome. Science (New York, N.Y.), 324(5928), 804-807.
27. Filonov, G. S., Piatkevich, K. D., Ting, L.-M., Zhang, J., Kim, K., & Verkhusha, V. V. (2011). Bright and stable near-infrared fluorescent protein for in vivo imaging. Nature Biotechnology, 29(8), 757-761.
28. Kumagai, A., Ando, R., Miyatake, H., Greimel, P., Kobayashi, T., Hirabayashi, Y. Miyawaki, A. (2013). A bilirubin-inducible fluorescent protein from eel muscle. Cell, 153(7), 1602-1611.
29. McIsaac, R. S., Engqvist, M. K. M., Wannier, T., Rosenthal, A. Z., Herwig, L., Flytzanis, N. C., Arnold, F. H. (2014). Directed evolution of a far-red fluorescent rhodopsin. Proceedings of the National Academy of Sciences, 105(17), 6374-9.
30. Yapici, I., Lee, K. S. S., Berbasova, T., Nosrati, M., Jia, X., Vasileiou, C., Borhan, B. (2015). "Turn-On" Protein Fluorescence: In Situ Formation of Cyanine Dyes. Journal of the American Chemical Society, 137(3), 1073-1080.
31. Shaner, N. C., Steinbach, P. A., & Tsien, R. Y. (2005). A guide to choosing fluorescent proteins. Nature Methods, 2(12), 905-909.
32. Allenmark, S. (2003). Induced circular dichroism by chiral molecular interaction. Chirality.
33. Smith, G. D., Lemke, C. T., & Howell, P. L. (2007). Substructure determination in multiwavelength anomalous diffraction, single anomalous diffraction, and single isomorphous replacement with anomalous scattering data using Shake-and-Bake. Methods in Molecular Biology (Clifton, N.J.), 364,183-196.
34. Son, S. K., Chapman, H. N., & Santra, R. (2011). Multiwavelength anomalous diffraction at high X-ray intensity. Physical Review Letters, 107(21).
35. Lodish H, Berk A, Zipursky S L, et al. Molecular Cell Biology. 4th edition. New York: W. H. Freeman; 2000. Section 17.7, Protein Glycosylation in the ER and Golgi Complex.
36. Varki A, Esko J D, Colley K J. Cellular Organization of Glycosylation. In: Varki A, Cummings R D, Esko J D, et al., editors. Essentials of Glycobiology. 2nd edition. Cold Spring Harbor (N.Y.): Cold Spring Harbor Laboratory Press; 2009. Chapter 3.
37. Toh, K. C., Stojkovic, E. A., van Stokkum, I. H. M., Moffat, K., & Kennis, J. T. M. (2010). Proton-transfer and hydrogen-bond interactions determine fluorescence quantum yield and photochemical efficiency of bacteriophytochrome. Proceedings of the National Academy of Sciences of the United States of America, 107(20), 9170-9175.
38. Salewski, J., Escobar, F. V., Kaminski, S., Von Stetten, D., Keidel, A., Rippers, Y., Hildebrandt, P. (2013). Structure of the BV cofactor in the Pfr state of bathy and prototypical phytochromes. Journal of Biological Chemistry, 288(23), 16800-16814.
39. Takala, H., Bjorling, A., Berntsson, O., Lehtivuori, H., Niebling, S., Hoernke, M., Westenhoff, S. (2014). Signal amplification and transduction in phytochrome photosensors. Nature, 509(7499), 245-8.
40. Samma, A. A., Johnson, C. K., Song, S., Alvarez, S., & Zimmer, M. (2010). On the origin of fluorescence in bacteriophytochrome infrared fluorescent proteins. Journal of Physical Chemistry B, 114(46), 15362-15369.
41. Seibeck, S., Borucki, B., Otto, H., Inomata, K., Khawn, H., Kinoshita, H., Heyn, M. P. (2007). Locked 5Zs-BV blocks the Meta-RA to Meta-RC transition in the functional cycle of bacteriophytochrome Agp1. FEBS Letters, 581(28), 5425-5429.
42. Meech, S. R., & Tonge, P. J. (2009). Excited state dynamics in the green fluorescent protein. Journal of Photochemistry and Photobiology a-Chemistry, 205(1), 1-11.
43. Henderson, J. N., Osborn, M. F., Koon, N., Gepshtein, R., Huppert, D., & Remington, S. J. (2009). Excited state proton transfer in the red fluorescent protein mKeima. Journal of the American Chemical Society, 131(37), 13212-13213.
44. Holden, H. M., Rypniewski, W. R., Law, J. H., & Rayment, I. (1987). The molecular structure of insecticyanin from the tobacco hornworm Manduca sexta L. at 2.6 A resolution. The EMBO Journal, 6(6), 1565-1570.
45. Huber, R., Schneider, M., Mayr, I., Müller, R., Deutzmann, R., Suter, F., Kayser, H. (1987). Molecular structure of the bilin binding protein (BBP) from *Pieris brassicae* after refinement at 2.0 A resolution. Journal of Molecular Biology, 198(3), 499-513.
46. Murphy, J. T., & Lagarias, J. C. (1997). The phytofluors: a new class of fluorescent protein probes. Current Biology, 7(11), 870-876.
47. Bhattacharya, S., Auldridge, M. E., Lehtivuori, H., Ihalainen, J. a., & Forest, K. T. (2014). Origins of Fluorescence in Evolved Bacteriophytochromes. Journal of Biological Chemistry, 289(46), 32144-32152.
48. Moffat, K. (2014). Time-resolved crystallography and protein design: signaling photoreceptors and optogenetics. Philosophical Transactions of The Royal Society B, 369, 20130568.
49. Yang, X., Ren, Z., Kuk, J., & Moffat, K. (2011). Temperature-scan cryocrystallography reveals reaction intermediates in bacteriophytochrome. Nature, 479 (7373), 428-32.
50. Piatkevich, K. D., Malashkevich, V. N., Morozova, K. S., Nemkovich, N. a, Almo, S. C., & Verkhusha, V. V. (2013). Extended Stokes shift in fluorescent proteins: chromophore-protein interactions in a near-infrared TagRFP675 variant. Scientific Reports, 3, 1847.
51. Chica, R. A., Moore, M. M., Allen, B. D., & Mayo, S. L. (2010). Generation of longer emission wavelength red fluorescent proteins using computationally designed libraries. Proceedings of the National Academy of Sciences of the United States of America, 107(47), 20257-20262.

52. Ghosh, S.; Yu, C.; Ferraro, D. J.; Sudha, S.; Samir, K. P.; Schaefer, W. F.; Gibson, D. T.; Ramaswamy, S. 2016. A Blue Protein with Red Fluorescence. Proceedings of the National Academy of Sciences of the United States of America, 113(41):11513-11518.

Example 2—Obtaining SFP Monomer Variants

In this example, we report our development of stable monomers of SFP having similar fluorescent properties to the tetrameric protein. The low quantum yield and tetramerization of SFP are undesirable characteristics for in vivo imaging. Hence, the monomeric variants of SFP described herein are useful for biological applications as small near-infrared biliverdin-inducible fluorescent tags and reflects a major breakthrough in the field.

A structure-based rational mutagenesis was used to develop monomeric proteins of Sandercyanin fluorescent protein (SFP). Based on the insights from 1.8 Å resolution crystal structure of the wild type tetrameric SFP the molecular details of inter-subunit interactions were determined. We generated mutations at single amino acid residues located at the dimeric interface of the tetrameric protein. A software program for automated design of mutagenic primers, PrimerX (available at bioinformatics.org/primerx/on the World Wide Web) was used for designing site specific mutagenesis oligos to disrupt the interactions at the dimeric interface of the wild type SFP. The wild type SFP gene cloned into pET21a vector (synthesized from GenScript) was used as a template. The whole vector polymerase chain reaction (Strategene quickchange protocol) was to generate the site directed mutants. Mutagenesis was confirmed by Sanger sequencing (NCBS sequencing facility). Oligonucleotides used to obtain the SFP monomer mutants are presented in Table 6.

All SFP variants were expressed using *E. coli* BL21* (DE3) cells. Briefly, each of the SFP monomer mutant genes in pET21a vector were transformed into BL21*(DE3) cells and selected on a LB agar plate containing ampicillin (100 μg/mL). For large scale expression, about 5 mL of the overnight grown primary culture was inoculated into 500 mL of LB medium containing 100 μg/mL ampicillin. Cells were grown at 37° C. until $OD_{600}$ nm reached to 0.6-0.7. Then, cells were induced using 0.2 mM isopropyl-thiogalactoside (IPTG). Post-induction cells were grown at 20° C. for 20 hours. Thereafter, cells were harvested by centrifugation at 6000 rpm for 10 minutes. Bacterial cell pellet containing SFP as insoluble protein was resuspended in a lysis buffer (20 mM Tris-HCl, pH 7.5, 10 mM EDTA and 1% TritonX). The resuspended cells were lysed by sonication (3 cycles of 3 minutes each with 10 seconds on and 30 seconds off pulses at 50% amplitude). The cell lysate was centrifuged for 30 minutes at 13,000 rpm to separate supernatant from the pellet. The pellet containing SFP as inclusion bodies (IBs) was further processed. IBs were re-suspended in a solution containing 5 M guanidine HCl, 50 mM CAPS, 0.5 mM phenylmethylsulfony fluoride (PMSF) and 1 mM DTT pH 7.5, and incubated at room temperature for solubilization. The solubilized inclusion bodies were refolded and further purified by gel-filtration chromatography. Thus, refolded purified SFP was checked using an analytical gel filtration column for oligomerization state and biliverdin (BV) binding by UV-visible absorbance and fluorescence spectroscopy (FIGS. 1A-1D).

Design of Monomeric SFP—To generate monomeric mutants of Sandercyanin, crystal structure of tetrameric SFP was used as a starting model. We found a number of interacting residues which hold the two-monomer interfaces tightly to form a tetramer. All residues were mutated to change the physical property of the amino acid, and in-turn, affect the nature of interaction holding the interface. Residues L135, A137 and S138 were observed to interact with biliverdin of neighboring subunits, which may be the primary cause of biliverdin-inducible tetramerization in wild-type SFP. Other residues, namely, N34, V71, V94, A111, I114 were involved in protein-protein interaction at the other interface. We also targeted some aromatic residues at the in close proximity to the ligand in the binding pocket to understand spectral changes due to mutation, however, few of them were obtained as monomers and retained binding to biliverdin. After screening a large number of proteins, we identified 18 monomeric mutants of SFP which have ability to bind biliverdin and show red near-infrared fluorescence with large Stokes shift. MonoSFPs are 18.6 kDa—smaller than other SFPs known to date. These characteristics make monoSFP useful as fluorescent protein tag and applicable for two-photon (2P) microscopy. Additionally, we solved the crystal structure of two monoSFP mutants mSFP1 (V71E) and mSFP2 (L135E) in complex with the ligand to understand structural changes due to monomerization and to verify success of our rational design methodology.

Figures 2A, 2B:
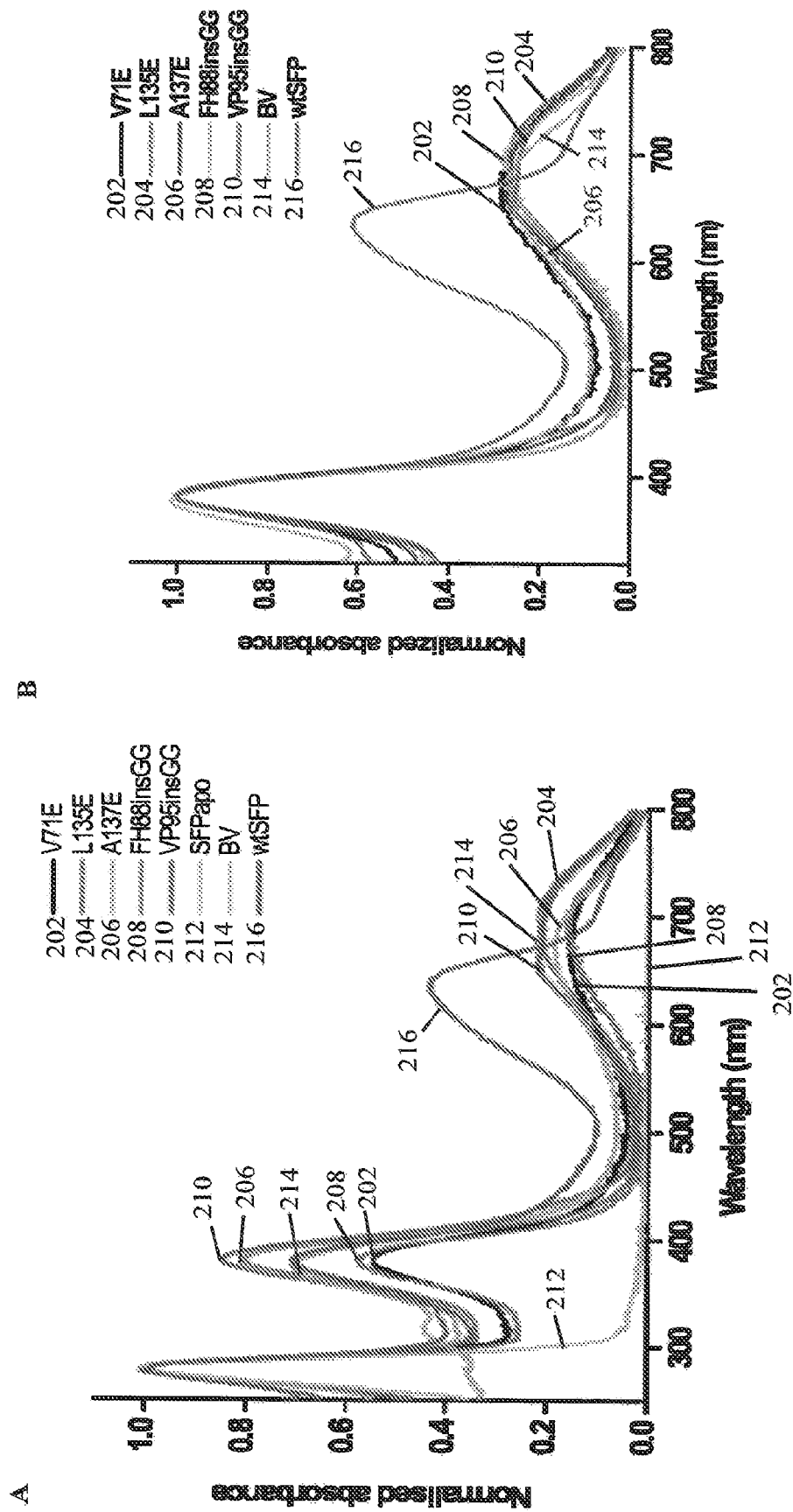
FIGS. 2A-2B are absorbance spectra of wild-type SFP and monomeric SFP variants (A) normalized to protein ($A_{280}$) and (B) formalized to biliverdin ($A_{380}$) spectra. Wild-type and monomeric SFP variants represented include V71E 202, L135E 204, A137E 206, FH88insGG 208, VP95insGG 210, SFPapo 212, free biliverdin (BV) 214, and wtSFP 216.

Characterization of monoSFP Variants—MonoSFP variants were characterized by size-exclusion chromatography during purification of the proteins. We further characterized the spectral properties and binding-efficiencies of a few of these monoSFPs (Tables 2 and 4), and found them to be similar to wild-type SFP (FIG. 2, FIG. 3, Table 4). They have far-red to near infra-red fluorescence with large Stokes shift. However, the quantum efficiency decreased significantly, making them less bright than tetrameric SFP. The decreased quantum efficiency could be caused by loss of tetramer formation, which may have exposed the bound ligand to a solvent molecule, hence scavenging the excess photon before relaxing to the ground state. To test this, we performed detergent (Triton X-100) assays with the monoSFPs and measured absorbance and fluorescence spectra. Further, we made attempts to extend one of the loops which encloses biliverdin in the centre of the protein. Two mutants, FH88insGG and VP95insGG, were extended with glycine residues at the 88th and 95th positions in the amino acid chain of L135E monoSFP mutant. One hypothesis was that extension would prevent photon loss due to solvent exposure of the ligand and enhance the quantum efficiency. These mutants retained binding to biliverdin and showed similar spectral properties, but did not show significantly increased brightness. These results suggested that glycine linkages may not be the best method of loop extension due to their increased flexibility and further modification is required for making the extended loop more stable and rigid.

Figures 5A, 5B, 5C, 5D, 5E, 5F:
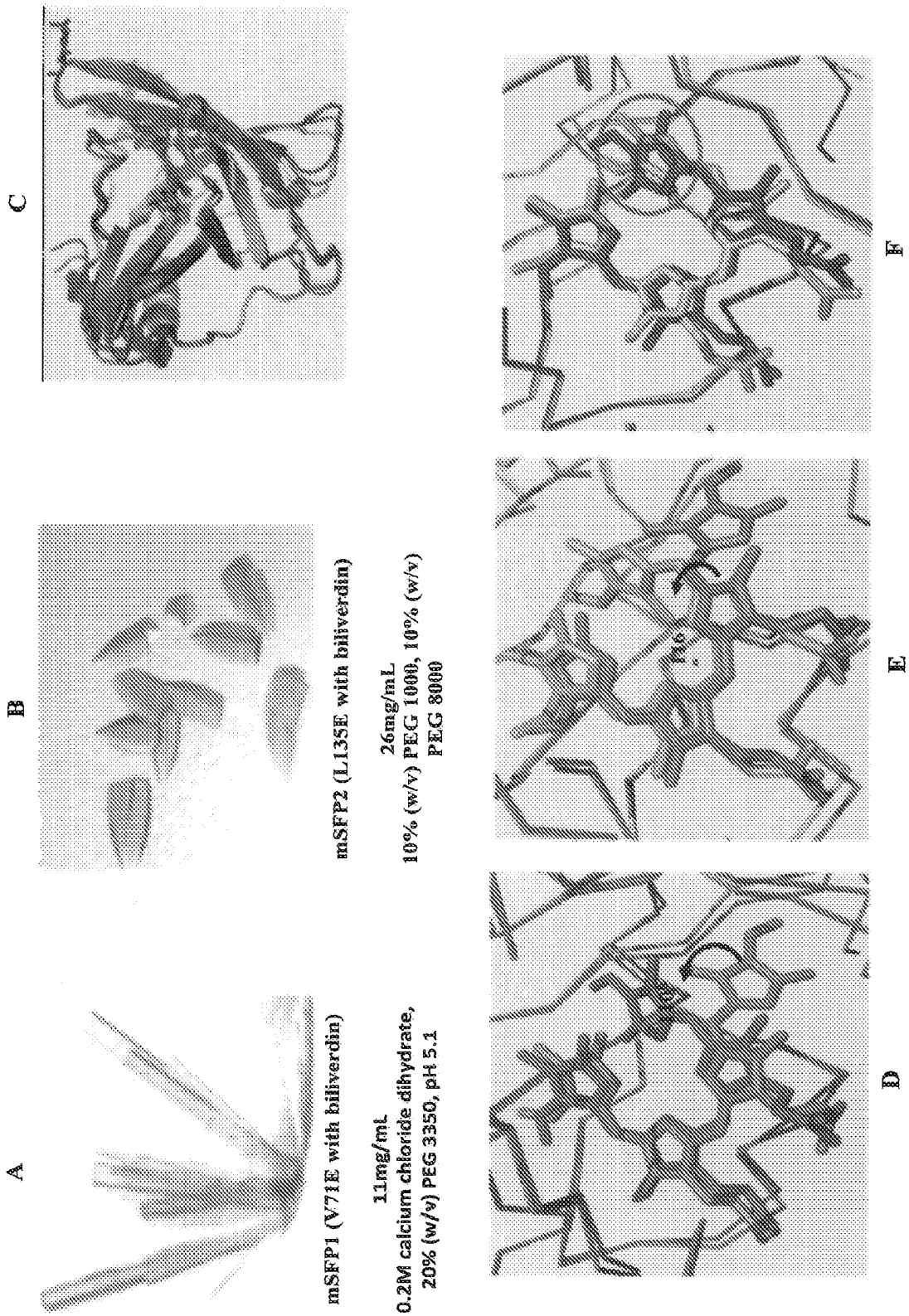
FIGS. 5A-5F show blue-green crystals of (A) mSFP1 and (B) mSFP2 in complex with biliverdin and the structure of wtSFP.

Crystals of two monoSFPs (mSFP1 and mSFP2) were obtained in different conditions (FIGS. 5A-5B) and their structure were solved at 2.5 Å and 2.7 Å using molecular replacement, with wild-type SFP structure as a template model. Structures of both monoSFPs showed a lipocalin fold forming a barrel, similar to the wild type (wt) SFP with insignificant difference in the secondary structure (FIG. 5C). Biliverdin is positioned in the centre of the barrel and surrounded by a large number of aromatic and hydrophobic residues stabilizing the chromophore. Overlap of crystal structures of wtSFP with the two monoSFPs show significant differences in the conformation of biliverdin as well as the orientation of neighboring aromatic residues surrounding the ligand in the binding pocket. D-ring pyrrole of biliverdin is seen to flip by 110° and 116° in mSFP1 and mSFP2 respectively (FIGS. 5D-5F) compared to biliverdin in wtSFP structure. Reviewing the spectral properties with changes in chromophore conformation, suggests that pyrrole D-ring rotation causes insignificant changes in modifying fluorescence properties of monoSFPs. The flipping of the ring may be caused by lack of vacant space in the monomer near the D-ring, due to absence of dimer interface. This may also cause solvent exposure of the chromophore in the bound state, leading to lowering of quantum yield compared to wtSFP. Detailed view of the crystal structure of monoSFPs also shows changes in the position of aromatic resides (FIG. 5F) F55, F106, H108, and Y142 which are important for stabilization of biliverdin due to stacking interactions.

TABLE 2

Monomeric SFP Variants Generated from Rational-Based Mutagenesis of Tetrameric SFP

| Mutant Name | Site of mutation | Binds to BV | Oligomeric state |
| --- | --- | --- | --- |
| mSFP-L135F | Dimer-interface | Y | monomer |
| mSFP-A137F | Dimer-interface | Y | monomer |
| mSFP-A111E | Dimer-interface | Y | monomer |
| mSFP-A111F | Dimer-interface | Y | monomer |
| mSFP-V95F | Dimer-interface | Y | monomer |
| mSFP-V95Y | Dimer-interface | Y | monomer |
| mSFP-I114Y | Dimer-interface | Y | monomer |
| mSFP-N34Y | Dimer-interface | Y | monomer |
| mSFP-N34F | Dimer-interface | Y | monomer |
| SFP-S138A | Dimer-interface | Y | monomer |
| SFP-Y142L | BV-binding pocket | Y | monomer |
| SFP-Y142I | BV-binding pocket | Y | monomer |
| SFP-Y116A | BV-binding pocket | Y | Monomer |

TABLE 3

Amino Acid Sequences of Monomeric SFP Variants

| | | |
| --- | --- | --- |
| mSFP-V71E | FIKPGRCPKPAVQEDFDAARYLGVWYDIQRLPNKFQKGECA TATYSLSPGEGFSVFNRERLANGTIKSVIGSAIAEDPCEPAKL QFFHENAAPVPYWVLSTDYDNYALVYSCINLGASHAAYASI VSRQPTLPEETIKKLQGTMSSFGVGVDTLLTTNQDAAYCSA MNQ | SEQ ID NO: 2 |
| mSFP-L135E | FIKPGRCPKPAVQEDFDAARYLGVWYDIQRLPNKFQKGECA TATYSLSPGVGFSVFNRERLANGTIKSVIGSAIAEDPCEPAKL QFFHENAAPVPYWVLSTDYDNYALVYSCINEGASHAAYASI VSRQPTLPEETIKKLQGTMSSFGVGVDTLLTTNQDAAYCSA MNQ | SEQ ID NO: 3 |
| mSFP-A137E | FIKPGRCPKPAVQEDFDAARYLGVWYDIQRLPNKFQKGECA TATYSLSPGVGFSVFNRERLANGTIKSVIGSAIAEDPCEPAKL QFFHENAAPVPYWVLSTDYDNYALVYSCINLGESHAAYASI VSRQPTLPEETIKKLQGTMSSFGVGVDTLLTTNQDAAYCSA MNQ | SEQ ID NO: 4 |
| SmFP-L135E, FH88-insGG | MFIKPGRCPKPAVQEDFDAARYLGVWYDIQRLPNKFQKGEC ATATYSLSPGVGFSVFNRERLANGTIKSVIGSAIAEDPCEPAK LQFGGFHENAAPVPYWVLSTDYDNYALVYSCINEGASHAAY ASIVSRQPTLPEETIKKLQGTMSSFGVGVDTLLTTNQDAAYC SAMNQ | SEQ ID NO: 5 |
| mSFP-L135E, VP95-insGG | MFIKPGRCPKPAVQEDFDAARYLGVWYDIQRLPNKFQKGEC ATATYSLSPGVGFSVFNRERLANGTIKSVIGSAIAEDPCEPAK LQFFHENAAPGGVPYWVLSTDYDNYALVYSCINSFEGASHA AYASIVSRQPTLPEETIKKLQGTMSSFGVGVDTLLTTNQDAA YCSAMNQ | SEQ ID NO: 6 |
| mSFP-V52E no signal peptide | MFIKPGRCPKPAVQEDFDAARYLGVWYDIQRLPNKFQKGEC ATATYSLSPGEGFSVFNRERLANGTIKSVIGSAIAEDPCEPAK LQFFHENAAPVPYWVLSTDYDNYALVYSCINLGASHAAYAS IVSRQPTLPEETIKKLQGTMSSFGVGVDTLLTTNQDAAYCSA MNQ | SEQ ID NO: 7 |

TABLE 4

Spectral Properties of Monomeric SFPs Relative to Tetrameric SFP

| Protein | Molecular weight | Ex/Em1 | Ex/Em1 | Kd | Quantum yield |
|---|---|---|---|---|---|
| Wild-type SFP | 74.5 kDa | 375/675 | 630/675 | 5-6 uM | 0.016 |
| SFP-V71E | 18.6 kDa | 380/670 | 600/660 | 4-6 uM | 0.003 |
| SFP-L135E | 18.6 kDa | 380/682 | 600/676 | 4-12 uM | 0.025 |
| SFP-A137E | 18.6 kDa | 380/663 | 580/653 | 3-5 uM | 0.003 |
| SFP-FH88insGG | 18.7 kDa | 380/663 | 570/653 | — | 0.002 |
| SFP-VP95insGG | 18.7 kDa | 380/657 | 570/653 | — | 0.003 |

TABLE 5

Data Collection and Refinement Statistics

| | Data Collection | |
|---|---|---|
| Crystal | mSFP1 (V71E) | mSFP (L135E) |
| Source | BM14, Grenoble | BM14, Grenoble |
| Resolution range (A°) | 36.56-2.5 (2.59-2.5) | 39.65-2.746 (2.844-2.746) |
| Space group | P 41 | P 41 |
| Cell dimensions | | |
| Unit cell | 38.466 38.466 117.601 90 90 90 | 39.652 39.652 118.914 90 90 90 |
| Total reflections | | |
| Unique reflections | 5921 (613) | 4788 (465) |
| Multiplicity | | |
| Completeness (%) | 99.83 (99.35) | 99.50 (96.07) |
| Mean I/sigma (I) | 15.49 (3.05) | 11.64 (2.37) |
| Wilson B-factor | 36.54 | 44.11 |
| R-sym | | |
| R-factor | 0.1763 (0.2754) | 0.2206 (0.2803) |
| R-free | 0.2395 (0.2394) | 0.2807 (0.3170) |
| Number of atoms | 1369 | 1317 |
| macromolecules | 1281 | 1271 |
| ligands | 43 | 43 |
| Water | 13 | 3 |
| Protein residues | 166 | 167 |
| RMS (bonds) | 0.020 | 0.004 |
| RMS (angles) | 1.65 | 0.85 |
| Ramachandran favored (%) | 93 | 91 |
| Ramachandran outliers (%) | 0.61 | 0.61 |
| Clashscore | 27.78 | 14.40 |
| Average B-factor | 26.30 | 49.40 |
| macromolecules | 26.30 | 49.40 |
| solvent | 24.90 | 41.20 |

*Statistics for the highest-resolution shell are shown in parentheses.

TABLE 6

Oligonucleotide Primers for Site-Directed Mutagenesis of Monomeric SFP

| | | | |
|---|---|---|---|
| SFP-L135E | Forward | CTACAGCTGCATCAACGAAGGTGCGAGCCATGCGG | SEQ ID NO: 8 |
| | Reverse | CCGCATGGCTCGCACCTTCGTTGATGCAGCTGTAG | SEQ ID NO: 9 |
| SFP-L135F | Forward | GGTCTACAGCTGCATCAACTTTGGTGCGAGCCATGCGGCG | SEQ ID NO: 10 |
| | Reverse | CGCCGCATGGCTCGCACCAAAGTTGATGCAGCTGTAGACC | SEQ ID NO: 11 |
| SFP-A137E | Forward | GCTGCATCAACCTCGGTGAAAGCCATGCGGCGTATGC | SEQ ID NO: 12 |
| | Reverse | GCATACGCCGCATGGCTTTCACCGAGGTTGATGCAGC | SEQ ID NO: 13 |
| SFP-A137F | Forward | CAGCTGCATCAACCTCGGTTTTAGCCATGCGGCGTATGCCAG | SEQ ID NO: 14 |
| | Reverse | CTGGCATACGCCGCATGGCTAAAACCGAGGTTGATGCAGCTG | SEQ ID NO: 15 |
| SFP-A111E | Forward | GCAGTTCTTCCATGAGAACGAAGCCCCTGTTCCTTACTGGGTG | SEQ ID NO: 16 |
| | Reverse | CACCCAGTAAGGAACAGGGGCTTCGTTCTCATGGAAGAACTGC | SEQ ID NO: 17 |

TABLE 6-continued

Oligonucleotide Primers for Site-Directed Mutagenesis of Monomeric SFP

| | | | |
|---|---|---|---|
| SFP-A111F | Forward | CTGCAGTTCTTCCATGAGAACTTCGCCCCTGTTCCTTACTGGGTG | SEQ ID NO: 18 |
| | Reverse | CACCCAGTAAGGAACAGGGGCGAAGTTCTCATGGAAGAACTGCAG | SEQ ID NO: 19 |
| SFP-V71E | Forward | CAGCTTGAGCCCTGGAGAAGGATTTAGTGTTTTCAAC | SEQ ID NO: 20 |
| | Reverse | GTTGAAAACACTAAATCCTTCTCCAGGGCTCAAGCTG | SEQ ID NO: 21 |
| SFP-FH88-insGG | Forward | C AAG CTG CAG TTC GGC GGC TTC CAT GAG AAC | SEQ ID NO: 22 |
| | Reverse | G TTC TCA TGG AAG CCG CCG AAC TGC AGC TTG | SEQ ID NO: 23 |
| SFP-VP95-insGG | Forward | AAC GCT GCC CCT GGC GGC GTT CCT TAC TGG | SEQ ID NO: 24 |
| | Reverse | CCA GTA AGG AAC GCC GCC AGG GGC AGC GTT | SEQ ID NO: 25 |

Example 3—Expression of Wild Type SFP and Monomeric SFP Variants in Mammalian Cell Lines HEK293 cells used for transient transfection were obtained from ATCC and maintained in DMEM medium (GIBCO) containing 10% of fetal bovine serum. All oligonucleotides used for cloning the SFP gene were obtained from the Sigma-Aldrich company.

Construct design: The SFP gene was cloned into pcDNA3.1(+) mammalian expression vector with a secretory signal sequence at the 5' end and a FLAG tag sequence at the 3' end. Oligonucleotides: 5'-cgcggatccatggcctccatggccgccgtgctgacctgggccctggccctgctgtccgccttctccgccacccaggccatgttcatcaagccaggaaga-3' (SEQ ID NO:26); 5'-gtacgatcctcgagttacttatcgtcgtcatccttgtaatccatggtggcctggttcatggcgctgc-3' (SEQ ID NO:27) were used as forward and reverse oligos for PCR amplifying the SFP gene. The forward oligo was designed such that it contained a human apolipoprotein-A5 secretory signal sequence (underlined) in frame with the SFP gene, while the reverse oligo contained base sequence encoding for FLAG tag (ATMDYKDDDDK) (SEQ ID NO:28) (bold and underlined).

Transient expression of SFP as a secretory protein: Frozen vial of HEK293 cells were thawed and grown in DMEM medium supplemented with 10% FBS at 37° C. in a 5% $CO_2$ humidified environment. After 24 hours of growth, cells were split equally into three culture flasks (T75) and grown further for 24 hours in DMEM medium. When cells were grown to about 70% confluence, cells were transfected with pcDNA3.1(+) plasmid containing either the wild type SFP gene or the monomeric mutant (V71E) gene. The pcDNA3.1(+) plasmid without SFP gene was also transfected separately as negative control (vector alone). Lipofectamine 2000 reagent (Invitrogen) was used for transfection. Post-transfection cells were grown further for 48 hours and harvested by separating culture supernatant (sup) from cells. The culture supernatants were concentrated using 10 kDa cut-off membranes and analyzed for the SFP expression.

Western blot analysis of culture supernatants: For the analysis of SFP expression, concentrated culture supernatants of the wild type SFP, the monomeric (V71E) mutant SFP, and the vector alone samples were run on a 15% SDS-PAGE gel and blotted onto a nitrocellulose membrane. The SFP was detected using rabbit anti-FLAG antibodies and HRP-conjugated goat anti-rabbit antibodies. Chemiluminescence signal was developed using ECL reagent from GE Healthcare.

Figure 6A:
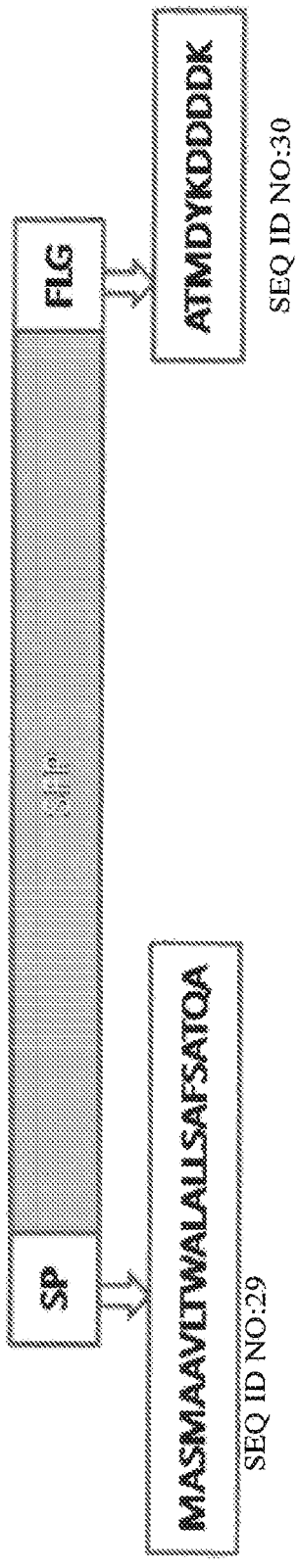
FIGS. 6A-6B show (A) construct design for expression of secretory SFP in mammalian cells and (B) mammalian expression of secreted SFP as detected by Western blot.
Figure 6B:
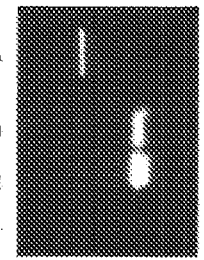

Results and Discussion: The human apolipoprotein-A5 secretory signal sequence (MASMAAVLTWALALL-SAFSATQA) (SEQ ID NO:29) was used for expressing SFP as a secreted protein. The expression construct was designed such that the secreted SFP contains a C-terminal FLAG tag (ATMDYKDDDDK) (SEQ ID NO:30). Anti-FLAG antibodies were used to detect the SFP in culture supernatants. As shown in FIG. 6A, SFP was expressed as a secreted protein. Culture supernatants of both the wild type and the monomeric variant (V71E) of the SFP expression samples show a band corresponding to SFP mass while the culture supernatant of vector alone (negative control), as expected, showed no expression of any SFP. See FIG. 6B. These results not only provide evidence toward expression of SFP in mammalian cells but also provide proof of concept data for use of SFP monomers as fusion tags.

Example 4—Increasing Brightness in SFP Monomers

Methods for increasing brightness in SFP monomers described herein include increasing hydrophobicity in the binding pocket, increasing binding affinity of biliverdin, covalent binding of the ligand, restriction of the conformational degrees of freedom of biliverdin, increasing 'flipping' of the D-ring of biliverdin, increasing loop size proximal to the biliverdin D-ring.

Brightness of the SFP monomer can be increased by increasing hydrophobicity by modifying residues in the binding pocket. There are 20 amino acids within 5 Å of biliverdin (BLA) in the binding pocket of Sandercyanin (SFP). These residues include Asp-47, Phe-55, Lys-57, Ala-61, Thr-62, Tyr-65, Ala-63, Asn-77, Arg-78, Glu-79, Lys-87, Ser-87, Val-89, Phe-106, His-108, Tyr-116, Val-129, Ser-131, Tyr-142 and Val 144. Substitution of polar residues (Asp-47, Lys-57, Ala-61, Thr-62, Tyr-65, Glu-79, Lys-87, Ser-87, Tyr-116, Ser-131 and Tyr-142) to hydrophobic amino acids (like Val, Leu, Ile, Phe) will increase the quantum yield of monomeric Sandercyanin. (Front Mol Biosci. 2015, 2:65; "Removal of Chromophore-Proximal Polar Atoms Decreases Water Content and Increases Fluorescence in a Near Infrared Phytofluor;" Proc Natl Acad Sci USA. 2(010); "Generation of longer emission wavelength red fluorescent proteins using computationally designed libraries.") A table of these substitutions is included below.

| Residue name and number | Position in the protein | Possible substitution/ mutation | nature of substitution/ mutation | Effect on the spectral properties |
|---|---|---|---|---|
| Asp-47 | BLA-binding pocket | Val, Leu, Ile, Phe | Hydrophobic amino acids | Enhanced quantum yield and red-shift in fluorescence |
| Lys-57 | BLA-binding pocket | Val, Leu, Ile, Phe | Hydrophobic amino acids | Enhanced quantum yield and red-shift in fluorescence |
| Ala-61 | BLA-binding pocket | Val, Leu, Ile, Phe | Hydrophobic amino acids | Enhanced quantum yield and red-shift in fluorescence |
| Thr-62 | BLA-binding pocket | Val, Leu, Ile, Phe | Hydrophobic amino acids | Enhanced quantum yield and red-shift in fluorescence |
| Tyr-65 | BLA-binding pocket | Val, Leu, Ile, Phe | Hydrophobic amino acids | Enhanced quantum yield and red-shift in fluorescence |
| Glu-79 | BLA-binding pocket | Val, Leu, Ile, Phe | Hydrophobic amino acids | Enhanced quantum yield and red-shift in fluorescence |
| Lys-87 | BLA-binding pocket | Val, Leu, Ile, Phe | Hydrophobic amino acids | Enhanced quantum yield and red-shift in fluorescence |
| Ser-88 | BLA-binding pocket | Val, Leu, Ile, Phe | Hydrophobic amino acids | Enhanced quantum yield and red-shift in fluorescence |
| Tyr-116 | BLA-binding pocket | Val, Leu, Ile, Phe | Hydrophobic amino acids | Enhanced quantum yield and red-shift in fluorescence |
| Ser-131 | BLA-binding pocket | Val, Leu, Ile, Phe | Hydrophobic amino acids | Enhanced quantum yield and red-shift in fluorescence |
| Tyr-142 | BLA-binding pocket | Val, Leu, Ile, Phe | Hydrophobic amino acids | Enhanced quantum yield and red-shift in fluorescence |
| Asn-77 | BLA-binding pocket | Val, Leu, Ile, Phe | Hydrophobic amino acids | Enhanced quantum yield and red-shift in fluorescence |
| Arg-78 | BLA-binding pocket | Val, Leu, Ile, Phe | Hydrophobic amino acids | Enhanced quantum yield and red-shift in fluorescence |
| His-108 | BLA-binding pocket | Val, Leu, Ile, Phe | Hydrophobic amino acids | Enhanced quantum yield and red-shift in fluorescence |

Figure 14:
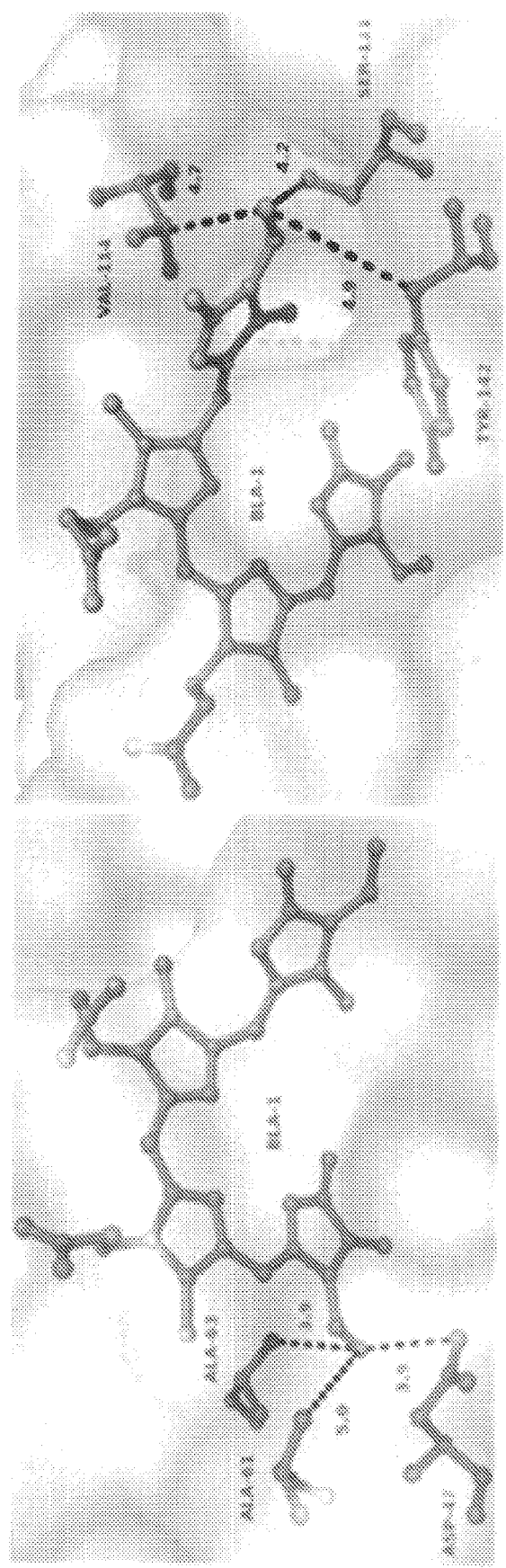
FIG. 14 show the BLA binding pocket in SFP. The left shows residues close to the A-ring of BLA in SFP, and the right shows residues close to the D-ring of BLA in SFP

Covalent linkage of the biliverdin within the binding pocket is also predicted to increase the brightness of the SFP monomer. Comparing crystal structures of SFP and bacteriophytochromes, we identified residues within 5 Å of A- and D-ring pyrrole of biliverdin to make a thioether covalent linkage between the vinyl group and apo-SFP via cysteine substitutions (FIG. 14). Topologically, the closest residues from A-ring on SFP to the cysteine residue in the phytochromes are Asp-47, Ala-61 and Ala-63. Similarly, Val-114, Ser-131 and Y-142 are close to the D-ring of biliverdin.

| Residue name and number | Position in the protein | Possible substitution/ mutation | purpose of substitution/ mutation | Effect on the spectral properties |
|---|---|---|---|---|
| Asp 47 | BLA-binding pocket, close to A-ring | Cys | Make covalent-thiother bond with BLA A-ring | Increased binding affinity |
| Ala 61 | BLA-binding pocket, close to A-ring | Cys | Make covalent-thiother bond with BLA A-ring | Increased binding affinity |
| Ala 63 | BLA-binding pocket, close to A-ring | Cys | Make covalent-thiother bond with BLA A-ring | Increased binding affinity |

Increasing the binding affinity of the biliverdin in the binding pocket is also proposed to increase the binding of the SFP monomer. One approach for increasing the binding affinity is to restrict the conformational degrees of freedom of biliverdin. This may be done by increasing pi-stacking interactions between the pyrrole rings of biliverdin and the side-chains of aromatic amino acids. ("Brighter Red Fluorescent Proteins by Rational Design of Triple-Decker Motif," ACS Chem Biol 2016 Feb. 19; 11(2):508-17; "Exploring color tuning strategies in red fluorescent proteins, Photochem Photobiol Sci. 2015 February; 14(2):200-12")

| Residue name and number | Position in the protein | Possible substitution/ mutation | nature of substitution/ mutation | Effect on the spectral properties |
|---|---|---|---|---|
| Asp-47 | BLA-binding pocket | Tyr, Phe | Aromatic amino acids | Increased binding affinity |
| Lys-57 | BLA-binding pocket | Tyr, Phe | Aromatic amino acids | Increased binding affinity |
| Ala-61 | BLA-binding pocket | Tyr, Phe | Aromatic amino acids | Increased binding affinity |
| Thr-62 | BLA-binding pocket | Tyr, Phe | Aromatic amino acids | Increased binding affinity |

-continued

| Residue name and number | Position in the protein | Possible substitution/mutation | nature of substitution/mutation | Effect on the spectral properties |
|---|---|---|---|---|
| Asn-77 | BLA-binding pocket | Tyr, Phe | Aromatic amino acids | Increased binding affinity |
| Arg-78 | BLA-binding pocket | Tyr, Phe | Aromatic amino acids | Increased binding affinity |
| G1u-79 | BLA-binding pocket | Tyr, Phe | Aromatic amino acids | Increased binding affinity |
| Lys-87 | BLA-binding pocket | Tyr, Phe | Aromatic amino acids | Increased binding affinity |
| Ser-88 | BLA-binding pocket | Tyr, Phe | Aromatic amino acids | Increased binding affinity |
| Ser-131 | BLA-binding pocket | Tyr, Phe | Aromatic amino acids | Increased binding affinity |
| His-108 | BLA-binding pocket | Tyr, Phe | Aromatic amino acids | Increased binding affinity |

Another strategy to increase the brightness of the SFP monomer is to encourage the flipping phenomenon. By "flipping phenomenon", we mean the isomerization of the D-ring of biliverdin around the C15-C16 bond. From the crystal structure of SFP, we have identified the aromatic amino acids in the vicinity of biliverdin which hinder the rotation of D-ring. These residues are Phe-106, His-108 and Tyr-142. Our studies show that His-108-Ala and Tyr-142-Ala permits flipping of D-ring of biliverdin. ("Trans-cis isomerization is responsible for the red-shifted fluorescence in variants of the red fluorescent protein eqFP611", J Am Chem Soc. 2008 Sep. 24; 130(38):12578-9, "Photoconversion in the red fluorescent protein from the sea anemone Entacmaea quadricolor: is cis-trans isomerization involved?" JACS, 2006, 128(19):6270-6271; "Optimized and far-red-emitting variants of fluorescent protein eqFP611," Chem Biol. 2008 March; 15(3):224-33; "Crystallographic structures of Discosoma red fluorescent protein with immature and mature chromophores: linking peptide bond trans-cis isomerization and acylimine formation in chromophore maturation," Biochemistry. 2005 Jul. 26; 44(29):9833-40.)

| Residue name and number | Position in the protein | Possible sub-stitution/mutation | purpose of sub-stitution/mutation | Effect on the spectral properties |
|---|---|---|---|---|
| Phe-106 | BLA-binding pocket, close to D-ring | Ala, Gly | Increasing conformational space near D-ring of BLA | Increase the flipping, reduced photobleaching |

-continued

| Residue name and number | Position in the protein | Possible sub-stitution/mutation | purpose of sub-stitution/mutation | Effect on the spectral properties |
|---|---|---|---|---|
| His-108 | BLA-binding pocket, close to D-ring | Ala, Gly | Increasing conformational space near D-ring of BLA | Increase the flipping, reduced photobleaching |
| Tyr- 142 | BLA-binding pocket, close to D-ring | Ala, Gly | Increasing conformational space near D-ring of BLA | Increase the flipping, reduced photobleaching |

Another strategy to increase the brightness of the SFP monomer is to increase the loop size which interacts with the D-ring of biliverdin. By increasing the loop size, biliverdin will be more tightly bound and the look will close which will in turn eliminate water molecules from the binding pocket which will increase the hydrophobicity. The SFP structure comprises multiple loops which enclose BLA in the beta-barrel in the lipocalin structure of the protein. Loops are important in connecting secondary structures in a protein. Since they are unstructured, they are highly dynamic in nature and mostly floppy. In SFP, there are loops close to the D-ring of BLA (H108-V114 and L135-S138) which stabilize the chromophore (BLA) in the protein. These loops also prevent excess solvent to enter BLA-binding pocket. Increasing the loop size maybe accomplished by, but is not limited to, insertion of amino acids immediately before, immediately after, or between H108 and V114 or L135 and S138, or by mutation of the amino acids in these loops to larger amino acids.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

We claim:

1. An isolated variant polypeptide of Sandercyanin fluorescent protein (SFP) having at least 95% sequence identity to SEQ ID NOs: 1 or 31 and further comprising at least one substitution selected from (i) a hydrophobic amino acid substitution at a position selected from the group consisting of D47, K57, A61, T62, Y65, N77, R78, E79, K87, S88, H108, Y116, S131, and Y142 as numbered relative to SEQ ID NO:1; (ii) a cysteine amino acid substitution at a position selected from the group consisting of D47, A61, and A63 as numbered relative to SEQ ID NO:1; (iii) an aromatic amino acid substitution at a position selected from the group consisting of D47, K57, A61, T62, N77, R78, E79, K87, S88, S131, and H108 as numbered relative to SEQ ID NO:1; (iv) an alanine or glycine substitution at a position selected from the group consisting of F106, H108, and Y142 as numbered relative to SEQ ID NO:1; and combinations thereof, wherein the variant has increased brightness compared to wild-type SFP of SEQ ID NO:1.

2. The variant polypeptide of claim 1, further comprising at least one amino acid substitution selected from the group consisting of V71E, L135E, L135F, A137E, A137F, A111E, and A111F relative to SEQ ID NO:1.

3. The variant polypeptide of claim 1, wherein the variant comprises a sequence selected from the group consisting of SEQ ID NO:2, SEQ ID NO:3, SEQ ID NO:4, SEQ ID NO:5, SEQ ID NO:6, and SEQ ID NO:7.

4. The variant polypeptide of claim 1, wherein the variant polypeptide exists primarily as a monomer.

5. The variant polypeptide of claim 1, wherein the polypeptide lacks the signal peptide of SEQ ID NO:32.

* * * * *

UNITED STATES PATENT AND TRADEMARK OFFICE
CERTIFICATE OF CORRECTION

PATENT NO. : 10,962,528 B2
APPLICATION NO. : 16/065277
DATED : March 30, 2021
INVENTOR(S) : Subramanian et al.

Page 1 of 1

It is certified that error appears in the above-identified patent and that said Letters Patent is hereby corrected as shown below:

In the Specification

Column 18, Line 41, "at 67 nm" should be --at 675 nm--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 32

<210> SEQ ID NO 1
<211> LENGTH: 189
<212> TYPE: PRT
<213> ORGANISM: Sander vitreus

<400> SEQUENCE: 1

Met Asn Ala Ile Gln Val Ile Ser Leu Thr Leu Leu Ser Val Leu Ala
1               5                   10                  15

Ala Lys Ala Met Phe Ile Lys Pro Gly Arg Cys Pro Lys Pro Ala Val
            20                  25                  30
```

```
Gln Glu Asp Phe Asp Ala Ala Arg Tyr Leu Gly Val Trp Tyr Asp Ile
         35                  40                  45

Gln Arg Leu Pro Asn Lys Phe Gln Lys Gly Glu Cys Ala Thr Ala Thr
 50                  55                  60

Tyr Ser Leu Ser Pro Gly Val Gly Phe Ser Val Phe Asn Arg Glu Arg
 65                  70                  75                  80

Leu Ala Asn Gly Thr Ile Lys Ser Val Ile Gly Ser Ala Ile Ala Glu
                 85                  90                  95

Asp Pro Cys Glu Pro Ala Lys Leu Gln Phe Phe His Glu Asn Ala Ala
             100                 105                 110

Pro Val Pro Tyr Trp Val Leu Ser Thr Asp Tyr Asp Asn Tyr Ala Leu
         115                 120                 125

Val Tyr Ser Cys Ile Asn Leu Gly Ala Ser His Ala Ala Tyr Ala Ser
 130                 135                 140

Ile Val Ser Arg Gln Pro Thr Leu Pro Glu Glu Thr Ile Lys Lys Leu
145                 150                 155                 160

Gln Gly Thr Met Ser Ser Phe Gly Val Gly Val Asp Thr Leu Leu Thr
                 165                 170                 175

Thr Asn Gln Asp Ala Ala Tyr Cys Ser Ala Met Ala Gln
            180                 185

<210> SEQ ID NO 2
<211> LENGTH: 169
<212> TYPE: PRT
<213> ORGANISM: Artificial Sequence
<220> FEATURE:
<223> OTHER INFORMATION: Synthetic

<400> SEQUENCE: 2

Phe Ile Lys Pro Gly Arg Cys Pro Lys Pro Ala Val Gln Glu Asp Phe
 1               5                  10                  15

Asp Ala Ala Arg Tyr Leu Gly Val Trp Tyr Asp Ile Gln Arg Leu Pro
                 20                  25                  30

Asn Lys Phe Gln Lys Gly Glu Cys Ala Thr Ala Thr Tyr Ser Leu Ser
             35                  40                  45

Pro Gly Glu Gly Phe Ser Val Phe Asn Arg Glu Arg Leu Ala Asn Gly
 50                  55                  60

Thr Ile Lys Ser Val Ile Gly Ser Ala Ile Ala Glu Asp Pro Cys Glu
 65                  70                  75                  80

Pro Ala Lys Leu Gln Phe Phe His Glu Asn Ala Ala Pro Val Pro Tyr
                 85                  90                  95

Trp Val Leu Ser Thr Asp Tyr Asp Asn Tyr Ala Leu Val Tyr Ser Cys
             100                 105                 110

Ile Asn Leu Gly Ala Ser His Ala Ala Tyr Ala Ser Ile Val Ser Arg
         115                 120                 125

Gln Pro Thr Leu Pro Glu Glu Thr Ile Lys Lys Leu Gln Gly Thr Met
 130                 135                 140

Ser Ser Phe Gly Val Gly Val Asp Thr Leu Leu Thr Thr Asn Gln Asp
145                 150                 155                 160

Ala Ala Tyr Cys Ser Ala Met Asn Gln
                 165

<210> SEQ ID NO 3
<211> LENGTH: 169
<212> TYPE: PRT
<213> ORGANISM: Artificial Sequence
```

<220> FEATURE:
<223> OTHER INFORMATION: synthetic

<400> SEQUENCE: 3

Phe Ile Lys Pro Gly Arg Cys Pro Lys Pro Ala Val Gln Glu Asp Phe
1               5                   10                  15

Asp Ala Ala Arg Tyr Leu Gly Val Trp Tyr Asp Ile Gln Arg Leu Pro
            20                  25                  30

Asn Lys Phe Gln Lys Gly Glu Cys Ala Thr Ala Thr Tyr Ser Leu Ser
        35                  40                  45

Pro Gly Val Gly Phe Ser Val Phe Asn Arg Glu Arg Leu Ala Asn Gly
    50                  55                  60

Thr Ile Lys Ser Val Ile Gly Ser Ala Ile Ala Glu Asp Pro Cys Glu
65                  70                  75                  80

Pro Ala Lys Leu Gln Phe Phe His Glu Asn Ala Ala Pro Val Pro Tyr
                85                  90                  95

Trp Val Leu Ser Thr Asp Tyr Asp Asn Tyr Ala Leu Val Tyr Ser Cys
            100                 105                 110

Ile Asn Glu Gly Ala Ser His Ala Ala Tyr Ala Ser Ile Val Ser Arg
            115                 120                 125

Gln Pro Thr Leu Pro Glu Glu Thr Ile Lys Lys Leu Gln Gly Thr Met
130                 135                 140

Ser Ser Phe Gly Val Gly Val Asp Thr Leu Leu Thr Thr Asn Gln Asp
145                 150                 155                 160

Ala Ala Tyr Cys Ser Ala Met Asn Gln
                165

<210> SEQ ID NO 4
<211> LENGTH: 169
<212> TYPE: PRT
<213> ORGANISM: Artificial Sequence
<220> FEATURE:
<223> OTHER INFORMATION: synthetic

<400> SEQUENCE: 4

Phe Ile Lys Pro Gly Arg Cys Pro Lys Pro Ala Val Gln Glu Asp Phe
1               5                   10                  15

Asp Ala Ala Arg Tyr Leu Gly Val Trp Tyr Asp Ile Gln Arg Leu Pro
            20                  25                  30

Asn Lys Phe Gln Lys Gly Glu Cys Ala Thr Ala Thr Tyr Ser Leu Ser
        35                  40                  45

Pro Gly Val Gly Phe Ser Val Phe Asn Arg Glu Arg Leu Ala Asn Gly
    50                  55                  60

Thr Ile Lys Ser Val Ile Gly Ser Ala Ile Ala Glu Asp Pro Cys Glu
65                  70                  75                  80

Pro Ala Lys Leu Gln Phe Phe His Glu Asn Ala Ala Pro Val Pro Tyr
                85                  90                  95

Trp Val Leu Ser Thr Asp Tyr Asp Asn Tyr Ala Leu Val Tyr Ser Cys
            100                 105                 110

Ile Asn Leu Gly Glu Ser His Ala Ala Tyr Ala Ser Ile Val Ser Arg
            115                 120                 125

Gln Pro Thr Leu Pro Glu Glu Thr Ile Lys Lys Leu Gln Gly Thr Met
130                 135                 140

```
Ser Ser Phe Gly Val Gly Val Asp Thr Leu Thr Thr Asn Gln Asp
145                 150                 155                 160

Ala Ala Tyr Cys Ser Ala Met Asn Gln
                165
```

<210> SEQ ID NO 5
<211> LENGTH: 172
<212> TYPE: PRT
<213> ORGANISM: Artificial Sequence
<220> FEATURE:
<223> OTHER INFORMATION: synthetic

<400> SEQUENCE: 5

```
Met Phe Ile Lys Pro Gly Arg Cys Pro Lys Pro Ala Val Gln Glu Asp
1               5                   10                  15

Phe Asp Ala Ala Arg Tyr Leu Gly Val Trp Tyr Asp Ile Gln Arg Leu
                20                  25                  30

Pro Asn Lys Phe Gln Lys Gly Glu Cys Ala Thr Ala Thr Tyr Ser Leu
            35                  40                  45

Ser Pro Gly Val Gly Phe Ser Val Phe Asn Arg Glu Arg Leu Ala Asn
        50                  55                  60

Gly Thr Ile Lys Ser Val Ile Gly Ser Ala Ile Ala Glu Asp Pro Cys
65                  70                  75                  80

Glu Pro Ala Lys Leu Gln Phe Gly Gly Phe His Glu Asn Ala Ala Pro
                85                  90                  95

Val Pro Tyr Trp Val Leu Ser Thr Asp Tyr Asp Asn Tyr Ala Leu Val
                100                 105                 110

Tyr Ser Cys Ile Asn Glu Gly Ala Ser His Ala Ala Tyr Ala Ser Ile
            115                 120                 125

Val Ser Arg Gln Pro Thr Leu Pro Glu Glu Thr Ile Lys Lys Leu Gln
130                 135                 140

Gly Thr Met Ser Ser Phe Gly Val Gly Val Asp Thr Leu Leu Thr Thr
145                 150                 155                 160

Asn Gln Asp Ala Ala Tyr Cys Ser Ala Met Asn Gln
                165                 170
```

<210> SEQ ID NO 6
<211> LENGTH: 174
<212> TYPE: PRT
<213> ORGANISM: Artificial Sequence
<220> FEATURE:
<223> OTHER INFORMATION: synthetic

<400> SEQUENCE: 6

```
Met Phe Ile Lys Pro Gly Arg Cys Pro Lys Pro Ala Val Gln Glu Asp
1               5                   10                  15

Phe Asp Ala Ala Arg Tyr Leu Gly Val Trp Tyr Asp Ile Gln Arg Leu
                20                  25                  30

Pro Asn Lys Phe Gln Lys Gly Glu Cys Ala Thr Ala Thr Tyr Ser Leu
            35                  40                  45

Ser Pro Gly Val Gly Phe Ser Val Phe Asn Arg Glu Arg Leu Ala Asn
        50                  55                  60

Gly Thr Ile Lys Ser Val Ile Gly Ser Ala Ile Ala Glu Asp Pro Cys
65                  70                  75                  80

Glu Pro Ala Lys Leu Gln Phe Phe His Glu Asn Ala Ala Pro Gly Gly
                85                  90                  95

Val Pro Tyr Trp Val Leu Ser Thr Asp Tyr Asp Asn Tyr Ala Leu Val
                100                 105                 110
```

```
Tyr Ser Cys Ile Asn Ser Phe Glu Gly Ala Ser His Ala Ala Tyr Ala
            115                 120                 125

Ser Ile Val Ser Arg Gln Pro Thr Leu Pro Glu Glu Thr Ile Lys Lys
    130                 135                 140

Leu Gln Gly Thr Met Ser Ser Phe Gly Val Gly Val Asp Thr Leu Leu
145                 150                 155                 160

Thr Thr Asn Gln Asp Ala Ala Tyr Cys Ser Ala Met Asn Gln
                165                 170

<210> SEQ ID NO 7
<211> LENGTH: 170
<212> TYPE: PRT
<213> ORGANISM: Artificial Sequence
<220> FEATURE:
<223> OTHER INFORMATION: synthetic

<400> SEQUENCE: 7

Met Phe Ile Lys Pro Gly Arg Cys Pro Lys Pro Ala Val Gln Glu Asp
1               5                   10                  15

Phe Asp Ala Ala Arg Tyr Leu Gly Val Trp Tyr Asp Ile Gln Arg Leu
                20                  25                  30

Pro Asn Lys Phe Gln Lys Gly Glu Cys Ala Thr Ala Thr Tyr Ser Leu
            35                  40                  45

Ser Pro Gly Glu Gly Phe Ser Val Phe Asn Arg Glu Arg Leu Ala Asn
    50                  55                  60

Gly Thr Ile Lys Ser Val Ile Gly Ser Ala Ile Ala Glu Asp Pro Cys
65                  70                  75                  80

Glu Pro Ala Lys Leu Gln Phe Phe His Glu Asn Ala Ala Pro Val Pro
                85                  90                  95

Tyr Trp Val Leu Ser Thr Asp Tyr Asp Asn Tyr Ala Leu Val Tyr Ser
            100                 105                 110

Cys Ile Asn Leu Gly Ala Ser His Ala Ala Tyr Ala Ser Ile Val Ser
            115                 120                 125

Arg Gln Pro Thr Leu Pro Glu Glu Thr Ile Lys Lys Leu Gln Gly Thr
    130                 135                 140

Met Ser Ser Phe Gly Val Gly Val Asp Thr Leu Leu Thr Thr Asn Gln
145                 150                 155                 160

Asp Ala Ala Tyr Cys Ser Ala Met Asn Gln
                165                 170

<210> SEQ ID NO 8
<211> LENGTH: 35
<212> TYPE: DNA
<213> ORGANISM: Artificial Sequence
<220> FEATURE:
<223> OTHER INFORMATION: synthetic

<400> SEQUENCE: 8
ctacagctgc atcaacgaag gtgcgagcca tgcgg                          35

<210> SEQ ID NO 9
<211> LENGTH: 35
<212> TYPE: DNA
<213> ORGANISM: Artificial Sequence
<220> FEATURE:
<223> OTHER INFORMATION: synthetic

<400> SEQUENCE: 9
ccgcatggct cgcaccttcg ttgatgcagc tgtag                          35
```

<210> SEQ ID NO 10
<211> LENGTH: 40
<212> TYPE: DNA
<213> ORGANISM: Artificial Sequence
<220> FEATURE:
<223> OTHER INFORMATION: synthetic

<400> SEQUENCE: 10
ggtctacagc tgcatcaact ttggtgcgag ccatgcggcg          40

<210> SEQ ID NO 11
<211> LENGTH: 40
<212> TYPE: DNA
<213> ORGANISM: Artificial Sequence
<220> FEATURE:
<223> OTHER INFORMATION: synthetic

<400> SEQUENCE: 11
cgccgcatgg ctcgcaccaa agttgatgca gctgtagacc          40

<210> SEQ ID NO 12
<211> LENGTH: 37
<212> TYPE: DNA
<213> ORGANISM: Artificial Sequence
<220> FEATURE:
<223> OTHER INFORMATION: synthetic

<400> SEQUENCE: 12
gctgcatcaa cctcggtgaa agccatgcgg cgtatgc             37

<210> SEQ ID NO 13
<211> LENGTH: 37
<212> TYPE: DNA
<213> ORGANISM: Artificial Sequence
<220> FEATURE:
<223> OTHER INFORMATION: synthetic

<400> SEQUENCE: 13
gcatacgccg catggctttc accgaggttg atgcagc             37

<210> SEQ ID NO 14
<211> LENGTH: 42
<212> TYPE: DNA
<213> ORGANISM: Artificial Sequence
<220> FEATURE:
<223> OTHER INFORMATION: synthetic

<400> SEQUENCE: 14
cagctgcatc aacctcggtt ttagccatgc ggcgtatgcc ag       42

<210> SEQ ID NO 15
<211> LENGTH: 42
<212> TYPE: DNA
<213> ORGANISM: Artificial Sequence
<220> FEATURE:
<223> OTHER INFORMATION: synthetic

<400> SEQUENCE: 15
ctggcatacg ccgcatggct aaaaccgagg ttgatgcagc tg       42

<210> SEQ ID NO 16
<211> LENGTH: 43
<212> TYPE: DNA
<213> ORGANISM: Artificial Sequence
<220> FEATURE:
<223> OTHER INFORMATION: synthetic

<400> SEQUENCE: 16
gcagttcttc catgagaacg aagcccctgt tccttactgg gtg                43

<210> SEQ ID NO 17
<211> LENGTH: 43
<212> TYPE: DNA
<213> ORGANISM: Artificial Sequence
<220> FEATURE:
<223> OTHER INFORMATION: synthetic

<400> SEQUENCE: 17
cacccagtaa ggaacagggg cttcgttctc atggagaac tgc                 43

<210> SEQ ID NO 18
<211> LENGTH: 45
<212> TYPE: DNA
<213> ORGANISM: Artificial Sequence
<220> FEATURE:
<223> OTHER INFORMATION: synthetic

<400> SEQUENCE: 18
ctgcagttct tccatgagaa cttcgcccct gttccttact gggtg              45

<210> SEQ ID NO 19
<211> LENGTH: 45
<212> TYPE: DNA
<213> ORGANISM: Artificial Sequence
<220> FEATURE:
<223> OTHER INFORMATION: synthetic

<400> SEQUENCE: 19
cacccagtaa ggaacagggg cgaagttctc atggagaac tgcag               45

<210> SEQ ID NO 20
<211> LENGTH: 37
<212> TYPE: DNA
<213> ORGANISM: Artificial Sequence
<220> FEATURE:
<223> OTHER INFORMATION: synthetic

<400> SEQUENCE: 20
cagcttgagc cctggagaag gatttagtgt tttcaac                       37

<210> SEQ ID NO 21
<211> LENGTH: 37
<212> TYPE: DNA
<213> ORGANISM: Artificial Sequence
<220> FEATURE:
<223> OTHER INFORMATION: synthetic

<400> SEQUENCE: 21
gttgaaaaca ctaaatcctt ctccagggct caagctg                       37

<210> SEQ ID NO 22
<211> LENGTH: 31
<212> TYPE: DNA
<213> ORGANISM: Artificial Sequence
<220> FEATURE:
<223> OTHER INFORMATION: synthetic

<400> SEQUENCE: 22
caagctgcag ttcggcggct tccatgagaa c                             31

<210> SEQ ID NO 23
<211> LENGTH: 31
<212> TYPE: DNA
<213> ORGANISM: Artificial Sequence
<220> FEATURE:
<223> OTHER INFORMATION: synthetic

<400> SEQUENCE: 23
gttctcatgg aagccgccga actgcagctt g                          31

<210> SEQ ID NO 24
<211> LENGTH: 30
<212> TYPE: DNA
<213> ORGANISM: Artificial Sequence
<220> FEATURE:
<223> OTHER INFORMATION: synthetic

<400> SEQUENCE: 24
aacgctgccc ctggcggcgt tccttactgg                            30

<210> SEQ ID NO 25
<211> LENGTH: 30
<212> TYPE: DNA
<213> ORGANISM: Artificial Sequence
<220> FEATURE:
<223> OTHER INFORMATION: synthetic

<400> SEQUENCE: 25
ccagtaagga acgccgccag gggcagcgtt                            30

<210> SEQ ID NO 26
<211> LENGTH: 99
<212> TYPE: DNA
<213> ORGANISM: Artificial Sequence
<220> FEATURE:
<223> OTHER INFORMATION: synthetic

<400> SEQUENCE: 26
cgcggatcca tggcctccat ggccgccgtg ctgacctggg ccctggccct gctgtccgcc    60
ttctccgcca cccaggccat gttcatcaag ccaggaaga                          99

<210> SEQ ID NO 27
<211> LENGTH: 67
<212> TYPE: DNA
<213> ORGANISM: Artificial Sequence
<220> FEATURE:
<223> OTHER INFORMATION: synthetic

<400> SEQUENCE: 27
gtacgatcct cgagttactt atcgtcgtca tccttgtaat ccatggtggc ctggttcatg    60
gcgctgc                                                             67

<210> SEQ ID NO 28
<211> LENGTH: 11
<212> TYPE: PRT
<213> ORGANISM: Artificial Sequence
<220> FEATURE:
<223> OTHER INFORMATION: synthetic

<400> SEQUENCE: 28

Ala Thr Met Asp Tyr Lys Asp Asp Asp Asp Lys
1               5                   10

```
<210> SEQ ID NO 29
<211> LENGTH: 23
<212> TYPE: PRT
<213> ORGANISM: Homo sapiens

<400> SEQUENCE: 29

Met Ala Ser Met Ala Ala Val Leu Thr Trp Ala Leu Ala Leu Leu Ser
1               5                   10                  15

Ala Phe Ser Ala Thr Gln Ala
            20

<210> SEQ ID NO 30
<211> LENGTH: 11
<212> TYPE: PRT
<213> ORGANISM: Artificial Sequence
<220> FEATURE:
<223> OTHER INFORMATION: synthetic

<400> SEQUENCE: 30

Ala Thr Met Asp Tyr Lys Asp Asp Asp Lys
1               5                   10

<210> SEQ ID NO 31
<211> LENGTH: 170
<212> TYPE: PRT
<213> ORGANISM: Sander vitreus

<400> SEQUENCE: 31

Met Phe Ile Lys Pro Gly Arg Cys Pro Lys Pro Ala Val Gln Glu Asp
1               5                   10                  15

Phe Asp Ala Ala Arg Tyr Leu Gly Val Trp Tyr Asp Ile Gln Arg Leu
            20                  25                  30

Pro Asn Lys Phe Gln Lys Gly Glu Cys Ala Thr Ala Thr Tyr Ser Leu
        35                  40                  45

Ser Pro Gly Val Gly Phe Ser Val Phe Asn Arg Glu Arg Leu Ala Asn
    50                  55                  60

Gly Thr Ile Lys Ser Val Ile Gly Ser Ala Ile Ala Glu Asp Pro Cys
65                  70                  75                  80

Glu Pro Ala Lys Leu Gln Phe Phe His Glu Asn Ala Ala Pro Val Pro
                85                  90                  95

Tyr Trp Val Leu Ser Thr Asp Tyr Asp Asn Tyr Ala Leu Val Tyr Ser
            100                 105                 110

Cys Ile Asn Leu Gly Ala Ser His Ala Ala Tyr Ala Ser Ile Val Ser
        115                 120                 125

Arg Gln Pro Thr Leu Pro Glu Glu Thr Ile Lys Lys Leu Gln Gly Thr
    130                 135                 140

Met Ser Ser Phe Gly Val Gly Val Asp Thr Leu Leu Thr Thr Asn Gln
145                 150                 155                 160

Asp Ala Ala Tyr Cys Ser Ala Met Asn Gln
                165                 170

<210> SEQ ID NO 32
<211> LENGTH: 19
<212> TYPE: PRT
<213> ORGANISM: Sander vitreus
```

```
<400> SEQUENCE: 32

Met Asn Ala Ile Gln Val Ile Ser Leu Thr Leu Leu Ser Val Leu Ala
1               5                   10                  15

Ala Lys Ala
```